(12) United States Patent
Aoba et al.

(10) Patent No.: US 8,034,094 B2
(45) Date of Patent: Oct. 11, 2011

(54) STENT DELIVERY SYSTEM AND STENT DELIVERY METHOD

(75) Inventors: Daisuke Aoba, Tokyo (JP); Yutaka Yanuma, Tokyo (JP); Chika Miyajima, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 167 days.

(21) Appl. No.: 12/136,992

(22) Filed: Jun. 11, 2008

(65) Prior Publication Data

US 2009/0312829 A1 Dec. 17, 2009

(51) Int. Cl.
*A61F 2/06* (2006.01)
(52) U.S. Cl. .................................................... 623/1.11
(58) Field of Classification Search .................. 623/1.11, 623/1.12, 1.23; 606/108, 191, 194, 198, 606/200
See application file for complete search history.

(56) References Cited

U.S. PATENT DOCUMENTS

| 5,242,452 A | 9/1993 | Inoue |
| 5,334,185 A | 8/1994 | Giesy et al. |
| 5,405,378 A * | 4/1995 | Strecker ...................... 623/1.12 |
| 5,921,952 A | 7/1999 | Desmond, III et al. |
| 6,562,024 B2 | 5/2003 | Alvarez de Toledo et al. |
| 2001/0018574 A1 * | 8/2001 | Toledo et al. ............ 604/164.09 |
| 2002/0043313 A1 | 4/2002 | Statnikov |
| 2004/0049256 A1 | 3/2004 | Yee |
| 2005/0027305 A1 | 2/2005 | Shiu et al. |
| 2005/0085891 A1 | 4/2005 | Goto et al. |
| 2005/0085892 A1 | 4/2005 | Goto et al. |
| 2005/0119722 A1 | 6/2005 | Styrc et al. |
| 2006/0036307 A1 * | 2/2006 | Zarembo et al. ............... 607/122 |
| 2006/0184224 A1 * | 8/2006 | Angel ........................... 623/1.11 |
| 2006/0195117 A1 * | 8/2006 | Rucker et al. ................. 606/108 |
| 2007/0233223 A1 | 10/2007 | Styrc |

(Continued)

FOREIGN PATENT DOCUMENTS

EP 1 842 508 A1 10/2007

(Continued)

OTHER PUBLICATIONS

Extended Partial European Search Report dated Sep. 2, 2009.

(Continued)

*Primary Examiner* — Tom Hughes
*Assistant Examiner* — Katherine M Shi
(74) *Attorney, Agent, or Firm* — Scully, Scott, Murphy & Presser, P.C.

(57) ABSTRACT

A stent delivery system includes a tubular stent which is retained in a body cavity of a living body; a pusher tube, whose distal end contacts with a proximal end of the stent, which pushes and moves the stent to a distal end side; a filament which connects the stent with the pusher tube by the proximal end side of the filament being engaged with the pusher tube and by the distal end side of the filament stretching to the stent side so as to penetrate the peripheral wall of the stent; an engaging member which is engaged with a distal end portion of the filament penetrating the peripheral wall of the stent, and which keeps the connecting condition between the stent and the pusher tube by the filament; and a pulling member which pulls a distal end side of the filament into a proximal end side of the pusher tube when the engagement between the engaging member and the filament is released and the connection between the stent and the pusher tube is released.

9 Claims, 28 Drawing Sheets

U.S. PATENT DOCUMENTS

2009/0099640 A1    4/2009    Weng

FOREIGN PATENT DOCUMENTS

| EP | 1 867 305 A2 | 12/2007 |
| --- | --- | --- |
| WO | WO 98/08740 | 3/1998 |
| WO | WO 99/08740 | 2/1999 |
| WO | WO 2007/070792 A2 | 6/2007 |
| WO | WO 2007/115483 A1 | 10/2007 |

OTHER PUBLICATIONS

Extended Partial European Search Report dated Sep. 2, 2009.
U.S. Office Action issued Sep. 15, 2010, in related U.S. Appl. No. 11/454,821.

* cited by examiner

STENT DELIVERY SYSTEM AND STENT DELIVERY METHOD

BACKGROUND OF THE INVENTION

1. Field of the Invention

The present invention relates to a stent delivery system and a stent delivery method for indwelling a stent at a hollow site of a digestive system, respiratory system, urinary system, reproductive system or the like by using an endoscope.

2. Background Art

Stents are used for obtaining a path that restores the function of an organ having a structure or a blockade having occurred somewhere in the hollow organs such as the digestive system, the respiratory system, the urinary system or the reproductive system.

In many cases in recent years, a maneuver of disposing a stent to a site of the aforementioned hollow organ which must be treated uses an endoscope and a specific treatment instrument. For example, U.S. Pat. No. 5,921,952 discloses a stent delivery system which is used for such maneuver. Specifically, it is provided with a guide catheter, a guidewire, a pusher tube and a suture (a filament) for connecting a stent to a distal end of the pusher tube in a manner that the stent can be removed. The guide catheter inserted in an inner hollow portion of the stent and is inserted in a living body together with the stent. The guidewire is inserted in the inner hollow portion of the guide catheter and guides the guide catheter and the stent in the living body. The pusher tube, of which the guide catheter is inserted in the inner hollow portion, is inserted in the living body together with the guide catheter and presses the stent along the guide catheter. The suture is passed through a hole which is formed in the distal end of the pusher tube, and both ends of the suture are tied so as to make a ring. In addition, a part of the suture is passed through the inner hollow portion of the stent through the hole which is formed in the stent and is forming a loop. The distal end of the guide catheter inserted in this loop prevents the suture from being detached from the stent. That is, the stent is connected to the distal end of the pusher tube via the suture detachably.

First in the procedure, four members combined like the above, i.e. the stent, the guide catheter, the pusher tube and the suture, are inserted into a channel which is formed along the guidewire in the inserting portion of the endoscope, and are protruded from the distal end of the inserting portion, and then the distal end of the stent and the guide catheter is inserted in the portion of the hollow organ where the treatment is necessary.

Subsequently, the guide catheter is pulled from a channel in the retracting direction while the guidewire and the pusher tube are maintained at a prescribed position. The guide catheter in this state may not have to be fully retracted. Drawing the guide catheter causes its distal end to be retracted from the loop of the suture, thereby releasing the stent from the guide catheter. Subsequently, the guidewire is pulled from the channel of the inserting portion of the endoscope in the retracting direction similarly to the guide catheter. The guidewire in this state may not have to be fully retracted. Drawing the guidewire causes its distal end to be retracted from the loop of the suture, thereby releasing the stent from the guide catheter, and releasing the engagement between the stent and the pusher tube via the suture.

Further pulling the pusher tube from the channel in the retracting direction causes the stent alone, which has previously been released from the pusher tube, to be indwelled at a site of the hollow organ which must be treated.

In the above-described procedure, when the distal end of the stent and the guide catheter is inserted in the portion of the hollow organ where the procedure is necessary, if the stent is arranged back from the portion where the procedure is necessary, the pusher tube is pulled a little before the guide catheter and the guidewire is pulled, that is, before the engaging relation between the stent and the pusher tube is released. This allows the stent connected to the distal end of the pusher tube to be returned to a desirable position.

SUMMARY OF THE INVENTION

An object of the present invention is to provide a stent delivery system and a stent delivery method for preventing a filament from being entangled with the stent inadvertently after releasing the connection between the stent and the pusher tube, and for preventing the stent from being connected fully or in some degree to the pusher tube again.

The stent delivery system according to an embodiment of the present invention includes a tubular stent which is retained in a body cavity of a living body; a pusher tube, whose distal end contacts with a proximal end of the stent, which pushes and moves the stent to a distal end side; a filament which connects the stent with the pusher tube by the proximal end side of the filament being engaged with the pusher tube and by the distal end side of the filament stretching to the stent side so as to penetrate the peripheral wall of the stent; an engaging member which is engaged with a distal end portion of the filament penetrating the peripheral wall of the stent, and which keeps the connecting condition between the stent and the pusher tube by the filament; and a pulling member which pulls a distal end side of the filament into a proximal end side of the pusher tube when the engagement between the engaging member and the filament is released and the connection between the stent and the pusher tube is released.

The stent delivery method according to an embodiment of the present invention includes a moving step in which a stent which is going to be left in a body cavity is pushed in with a pusher tube to a predetermined position in the body; a releasing step in which the engagement in a distal end side of the filament which connects the stent with the pusher tube is released and the connection between the stent and the pusher tube is released; and a pulling step in which the distal end side of the filament is pulled in a proximal end side of the pusher tube after the releasing step of the engagement of the distal end side of the filament.

PREFERRED EMBODIMENTS

Hereinbelow, embodiments of the present invention in details shall be described.

Note that portions that are common in a plurality of embodiments mentioned below shall be designated by the same reference numbers, descriptions thereof shall be omitted.

First Embodiment

A first embodiment of the stent delivery system of the present invention shall be described with reference to FIGS. 1 to 16.

Figure 1:
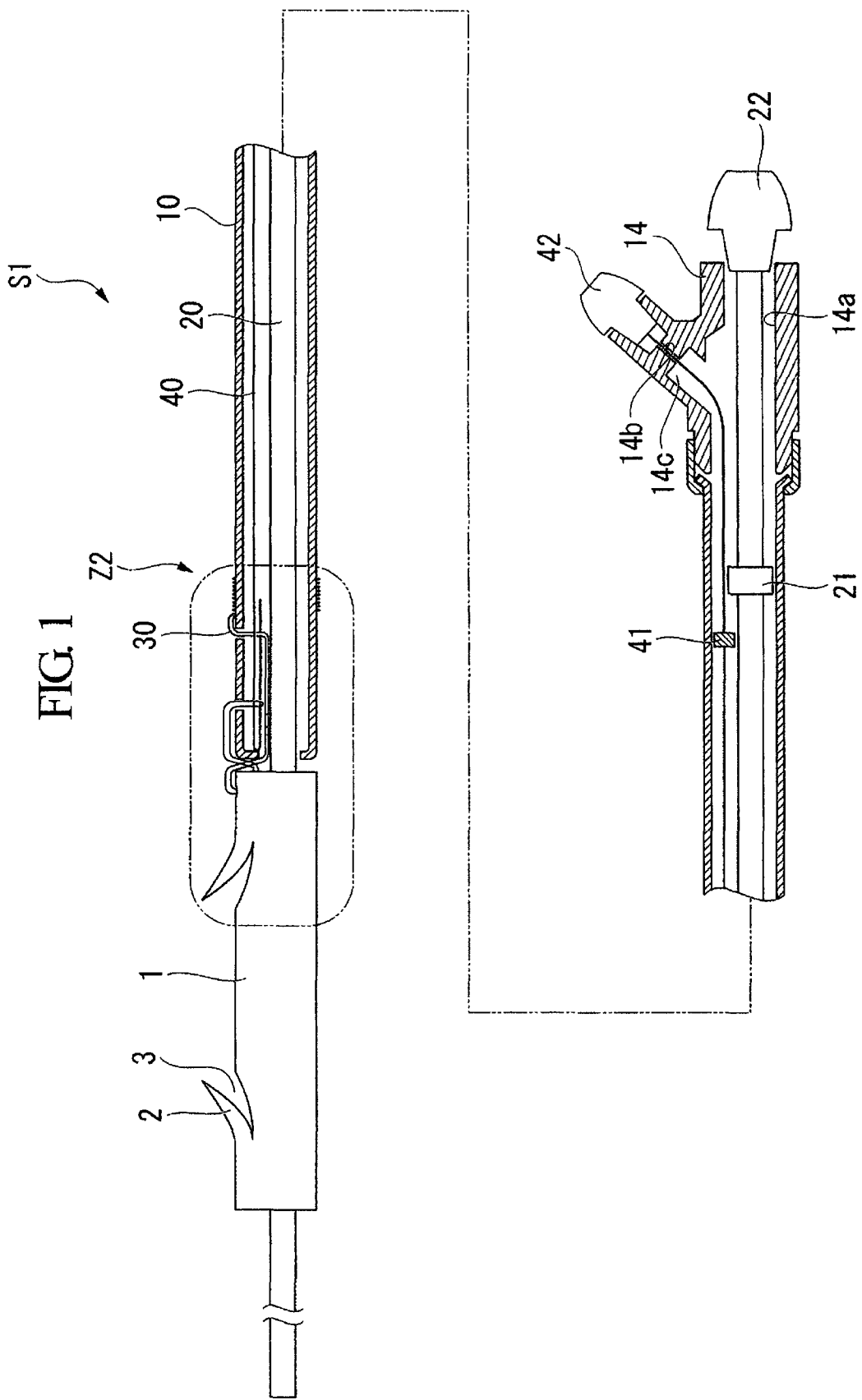
FIG. 1 is a partial cross-sectional view which shows the first embodiment of the stent delivery system of the present invention.

FIG. 1 is a partial cross-sectional view which shows the first embodiment of the stent delivery system of the present invention. As shown in this figure, a stent delivery system S1 is provided with a stent 1; a pusher tube 10 which pushes the proximal end of the stent 1 and moves the stent 1 distally; a guide catheter 20 which is passed through the hollow portions of the stent 1 and the pusher tube 10 freely retractable and extendable, and which guides them; a filament 30 which connects the stent 1 with the pusher tube 10; and a stilet 40 which engages the filament 30 and pulls the distal end of the filament 30 into the proximal end of the pusher tube 10 after the connection between the stent 1 and the pusher tube 10 is released. Note that the proximal end and the distal end are defined based on the guide catheter 20. That is, in FIG. 1, the left side indicates the distal end, and the right side indicates the proximal end.

Figure 2:
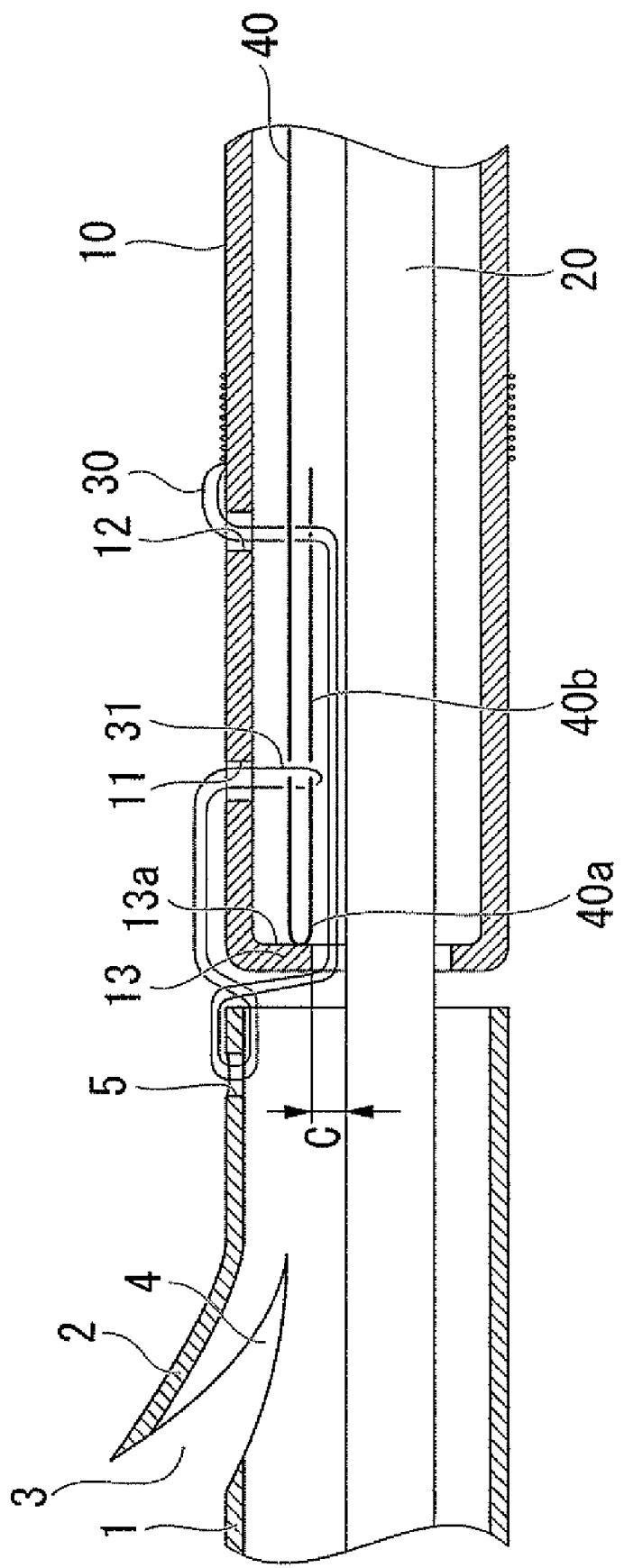
FIG. 2 is an enlarged cross-sectional view of Z2 part in FIG. 1.

FIG. 2 is an enlarged cross-sectional view which shows the connecting condition between the stent 1 and the pusher tube 10. As shown in this figure, the stent 1 is made of resin or metal, and formed in a tubular form. At two ends of the stent 1, a flap 2 is formed which holds the stent 1 by itself at a fixed position by engaging the stent 1 with the peripheral tissue of a living body when the stent 1 is inserted in the stricture site in the living body, and which functions as an anchor. The flap 2 is formed in the peripheral wall of the stent 1 by making a diagonal cut 3 which reaches the inner hollow portion of the stent 1. By making the cut 3, a through-hole 4 which pierces the inner peripheral surface from the outer peripheral surface is formed in the peripheral wall of the stent 1. In a more proximal end side of the peripheral wall which is provided with the flap 2 of the stent 1, a through-hole 5 which pierces the inner peripheral surface from the outer peripheral surface. This through-hole 5 is used to pass through the filament 30.

The pusher tube 10 is made of resin, and is formed flexible, elongate, and tubular. The pusher tube 10 is arranged at the proximal end side of the stent 1 so as to be coaxial with the stent 1. The guide catheter 20 is inserted in the inner hollow portion of the pusher tube 10. The guide catheter 20 is also inserted in the inner hollow portion of the stent 1 in the same way. This state of the distal end of the pusher tube 10 making contact with the proximal end of the stent 1 compresses and moves the stent 1 distally The inner diameter of the pusher tube 10 is set in a size so that the guide catheter 20 and the stilet 40 which are arranged in the inner hollow portion of the pusher tube 10 can move separately in the axial direction.

In the distal end portion of the pusher tube 10, two through-holes (the first and the second through-holes) 11 and 12 which are used to pass the filament 30 through are formed. The first through-hole 11 and the second through-hole 12 are formed at more proximally than the bent area of the pusher tube 10 when the pusher tube 10 is projected from the distal end of the inserting portion 60 of the endoscope in the procedure. In addition, the first through-hole 11 and the second through-hole 12 are formed so as to be separated in the longitudinal direction from the distal end to the proximal end of the pusher tube 10 and parallel to the axis of the pusher tube 10. The pusher tube 10 has the first through-hole 11 formed more distally relative to the second through-hole 12.

Also as shown in FIG. 2, a narrow portion 13 which narrows the opening at the distal end of the pusher tube 10 is formed in the distal end portion of the pusher tube 10 The narrow portion 13 is formed by making the whole peripheral surface curved so that the distal end of the peripheral wall of the pusher tube 10 is directed to the center of this tube. The size of a gap C between the inner end of the narrow portion 13 of the pusher tube 10 and the outer peripheral surface of the guide catheter 20 inserted in the hollow portion of the pusher tube 10 is set to be greater than the outer diameter of the filament 30 and smaller than the outer diameter of the stilet 40.

An operating-portion frame 14 is attached at the proximal end of the pusher tube 10. A hole 14a through which the proximal end side of the guide catheter 20 penetrates and a hole 14b through which the proximal end side of the stilet 40 penetrates in the upper side of this hole 14a are formed respectively in the operating-portion frame 14. A vacant portion 14c formed in the hole 14b and enclosing the second stopper 41 attached to the stilet 40 is formed at the position deviated the guide catheter 20.

The guide catheter 20 is a flexible-resin-made elongate and tubular component similarly to the pusher tube 10. The guide catheter 20 is passed through the inner hollow portion of the stent 1 and the pusher tube 10, and guides the stent 1 and the pusher tube 10 in the axial direction. The guide catheter 20 is inserted into a living body through the channel 61 of the inserting portion 60 of the endoscope together with the stent 1 and the pusher tube 10. The size of the inner diameter of the guide catheter 20 is set so that the guidewire 63 can be detachably inserted (Refer to FIGS. 9 to 11).

A contrastradiography portion, though not illustrated, is provided to the distal end of the guide catheter 20 if it is necessary to facilitate contrastradiography for the guide catheter 20. The first stopper 21 is attached to the outer periphery of the distal end of the guide catheter 20 which is covered by the pusher tube 10 when it is set in the channel of the inserting portion. The size of the first stopper 21 is set to be greater than the outer diameter of the guide catheter 20 and smaller than the inner diameter of the pusher tube 10. In addition, a cap 22, which is gripped by an operator when the guide catheter 20 is operated, is provided at the proximal end of the guide catheter 20.

A filament 30 is, for example, made of flexible resin or silk thread, and is fixed to the pusher tube 10 while the two ends thereof passed through the second through-hole 12 formed in the pusher tube are tied, glued, or being tied and glued, with the pusher tube 10. Therefore, the filament 30 is a ring. In the following descriptions, regarding the filament 30, the portion which is tied (or glued) with the pusher tube 10 is regarded as the proximal end, and the farthest portion from this proximal end is regarded as the distal end. A loop 31 is formed at the distal end of the filament 30.

The stilet 40 is constituted of a linear member, for example, a wire made of resin or metal, and is arranged between the inner peripheral surface of the pusher tube 10 and the outer peripheral surface of the guide catheter 20 inserted in the inner hollow portion 10a of the pusher tube 10 so as to be freely extending or retracting independently with respect to the guide catheter 20 in the axial direction. The distal end of the stilet 40 is bent in a U-letter shape. The bent distal end portion 40a is inserted through the loop 31 of the filament 30 detachably, and a part of the filament 30 is sandwiched in the bent fold-over portion 40b. Since the distal end portion 40a engages the loop 31 under the condition that the distal end portion 40a of the stilet 40 is inserted in the loop 31 of the filament 30, the filament 30 is prevented from being pulled out from the first through-hole 11 of the pusher tube 10. In addition, when the stilet 40 is moved proximally, the distal end portion 40a is pulled out from the loop 31 of the filament 30, and the engagement of the filament 30 by the distal end portion 40a is released. Furthermore, when the stilet 40 is moved proximally, the distal end section of the bent fold-over portion 40b of the stilet 40 engages with a part of the filament 30, and the distal end of the filament 30 is retracted into the proximal end of the pusher tube 10.

That is, the stilet 40 has two functions which are the function as an engaging member which keeps the connecting condition between the stent 1 and the pusher tube 10 by the filament 30, and the function as a pulling member which pulls the distal end side of the filament 30 in the proximal end side of the pusher tube.

Here, the material of the stilet 40 is chosen so that whole portions of the stilet 40 have higher stiffness than the filament 30.

A second stopper 41 is attached at the portion which is the outer periphery of the proximal end the stilet 40 and is covered with the pusher tube 10 when the stilet 400 is attached to a channel of the inserting portion. The size of the second stopper 41 is set to be greater than the outer diameter of the stilet 40 and smaller than the inner diameter of the pusher tube 10. In addition, the second stopper 41 is arranged more distally relative to the first stopper 21 attached in the guide catheter 20 in the inner hollow portion of the pusher tube 10. In addition, the second stopper 41 is arranged more distally of the hollow portion of the pusher tube 10 than the first stopper 21 which is attached to the guide catheter 20. Moreover, the outer diameter of the first stopper 21 is set in the inner hollow portion of the pusher tube 10 so as to interfere with the second stopper 41 each other, and thereby the second stopper 41 does not move over the first stopper 21 proximally. That is, the second stopper 41 and the first stopper 21 are in the interfering relation each other in the inner hollow portion of the pusher tube 10. When the stilet 40 is tried to move proximally before the guide catheter, it can be moved in a distance. However, when the guide catheter 20 is tried to move more, it cannot be moved since the second stopper 41 is bumped to the first stopper 21. But after the guide catheter 20 is moved proximally, the stilet 40 can be moved proximally since the first stopper 21 is moved proximally.

Figure 12:
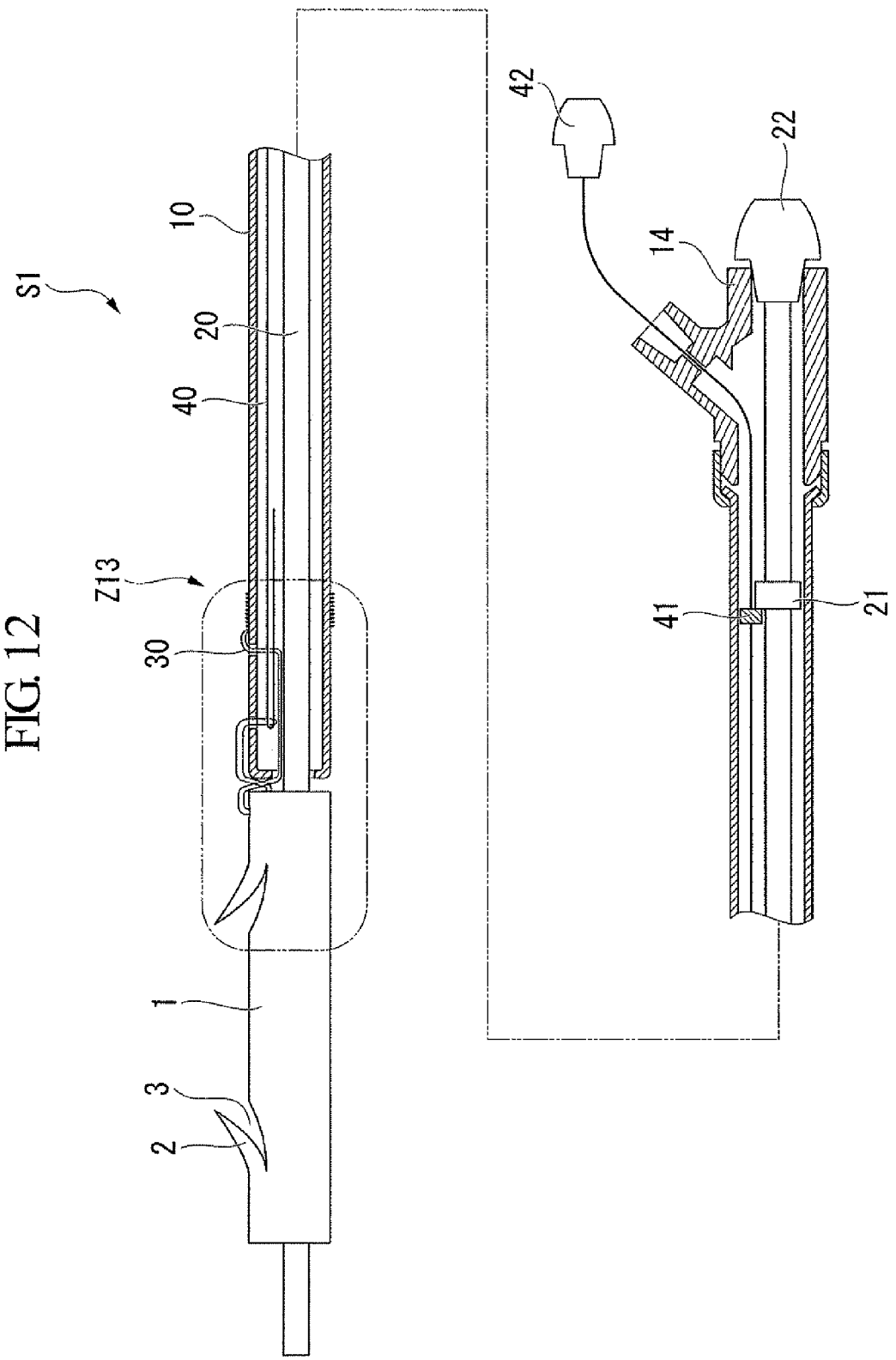
FIG. 12 shows the procedure of the manipulation which is conducted by the stent delivery system of the first embodiment, and shows the condition in which the stilet is going to be retreated at first.
Figure 13:
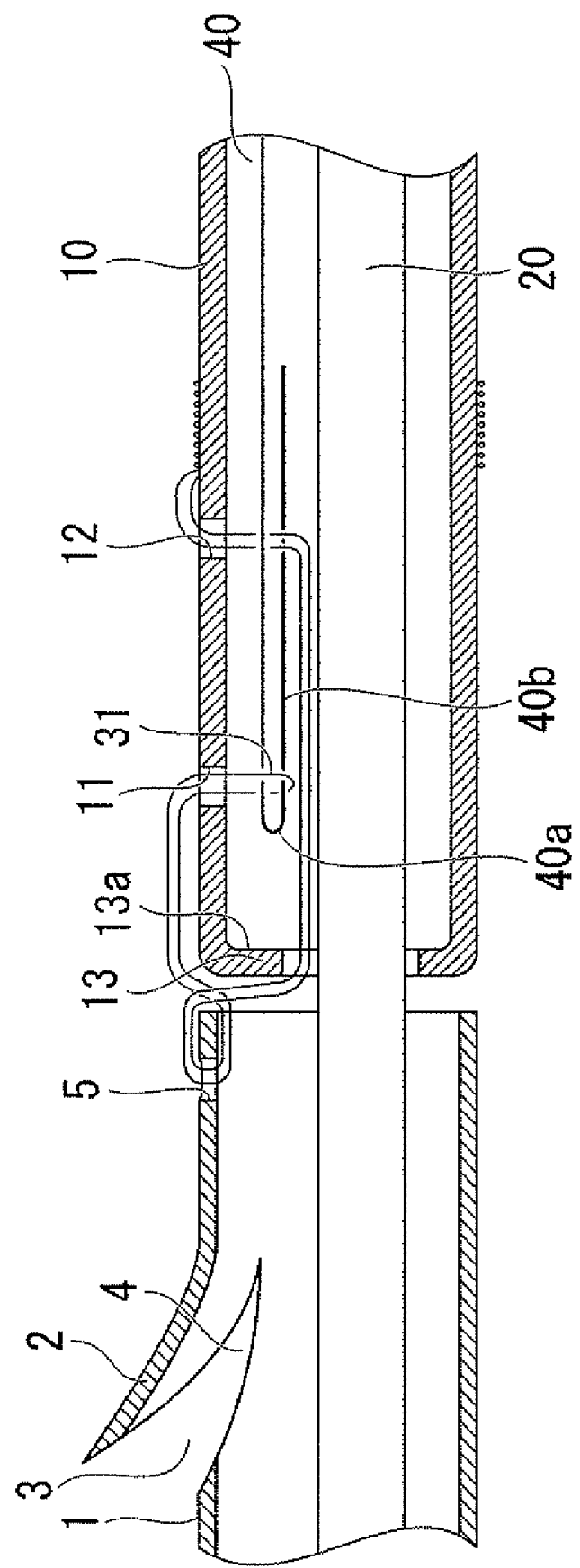
FIG. 13 is an enlarged cross-sectional view of Z13 part in FIG. 12.

The relative position of the first stopper 21 and the second stopper 41 as shown in FIGS. 12 and 13, is set so that the distal end portion 40a of the stilet 40 is positioned in more distally than the first through-hole 11 of the pusher tube 10 and is not able to be removed from the loop 31 of the filament 30 which penetrates the through-hole 11 when the stilet 40 is moved proximally before the guide catheter 20 and is in the condition that the second stopper 41 is bumped to the first stopper 21.

The proximal end of the stilet 40 is provided with the cap 42 which is gripped by the operator when the stilet 40 is manipulated to retreat. In addition, the length of the stilet 40 is set slightly longer than that of the pusher tube 10. Therefore, when the cap 42 is in the condition of being fitted to the receiver of the operating-portion frame 14, the distal end portion 40a of the stilet 40 is bumped slightly against the wall portion 13a of the narrow portion 13 of the pusher tube 10 by using the elasticity of the stilet 40 of itself Next, the connecting method between the stent 1 and the pusher tube 10 by the filament 30 shall be described with reference to FIG. 3 to FIG. 8.

Figure 3:
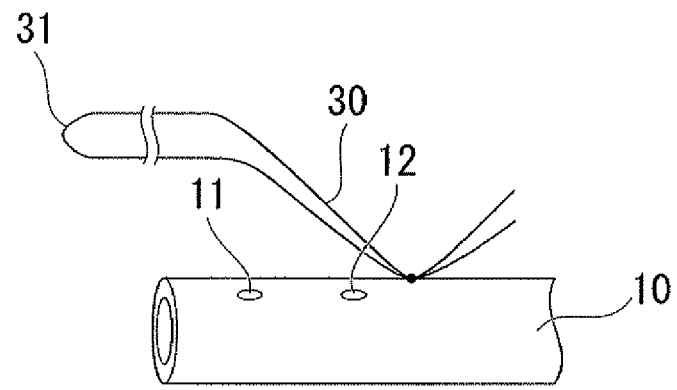
FIG. 3 is a perspective view which shows the connecting method between the stent and the pusher tube by the filament in the stent delivery system of the first embodiment.

As shown in FIG. 3, first, in a prescribed portion in the proximal end of the filament 30 is fixed temporarily to the portion which is outer periphery of the pusher tube 10 and is in the vicinity of the second through-hole 12 by such a suitable fixing means as glue or the like. The more distal end side of the filament 30 than the portion fixed temporarily is passed through the second through-hole 12 so as to be directed from the outer peripheral surface to the inner peripheral surface, and is made protruded to the outer direction out of the opening of the distal end side through the hollow portion of the pusher tube 10.

Figure 4:
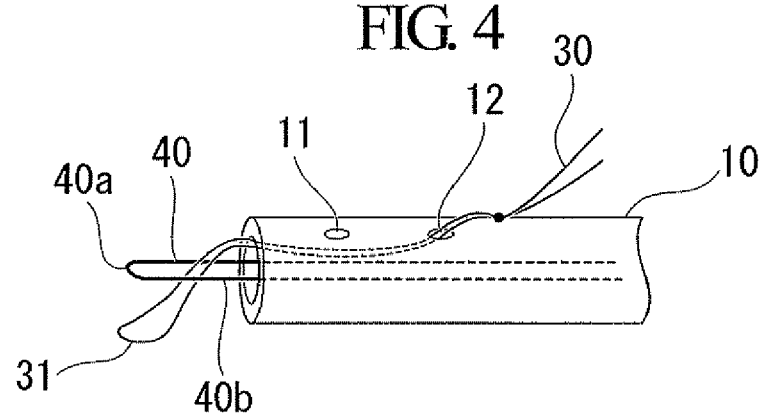
FIG. 4 is a perspective view which shows the connecting method between the stent and the pusher tube by the filament in the stent delivery system of the first embodiment

Next, as shown in FIG. 4, the bent distal end portion 40a of the stilet 40 to have been made insert beforehand is made protrude to the outer direction out of the opening of the distal end side of the pusher tube 10. The loop 31 of the filament 30 is passed through the bent fold-over portion 40b of the stilet 40 which is made protrude.

Figure 5:
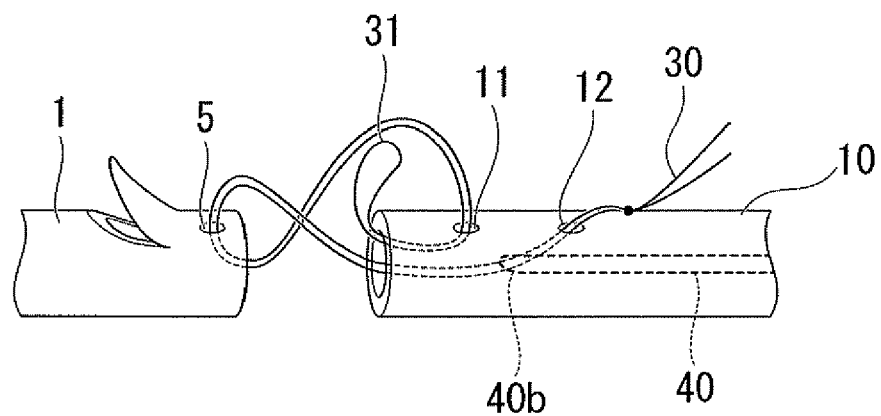
FIG. 5 is a perspective view which shows the connecting method between the stent and the pusher tube by the filament in the stent delivery system of the first embodiment.

Next, as shown in FIG. 5, the stilet 40 is pulled in the proximal end side and the distal end portion 40a is returned in the hollow portion of the pusher tube 10. Concurrently with this operation, the loop 31 is passed through the through-hole 5 of the stent 1 so as to be directed from the outer peripheral surface to the inner peripheral surface, and after that, the loop 31 is bent proximally and is pulled out from the opening of the proximal end side of the stent 1 to the outer direction. In this time, the filament 30 is wrapped around between the proximal end of the stent 1 and the through-hole 5 formed in the peripheral wall so as to form a circumference. Additionally, the loop 31 which has been pulled out is passed through the first through-hole 10 of the pusher tube 11 so as to be directed from the outer peripheral surface to the inner peripheral surface. The loop 31 after being passed through the first through-hole 11 is bent to the distal end side of the pusher tube 10, and is made protruded to the outer direction out of the opening of the distal end side.

Figure 6:
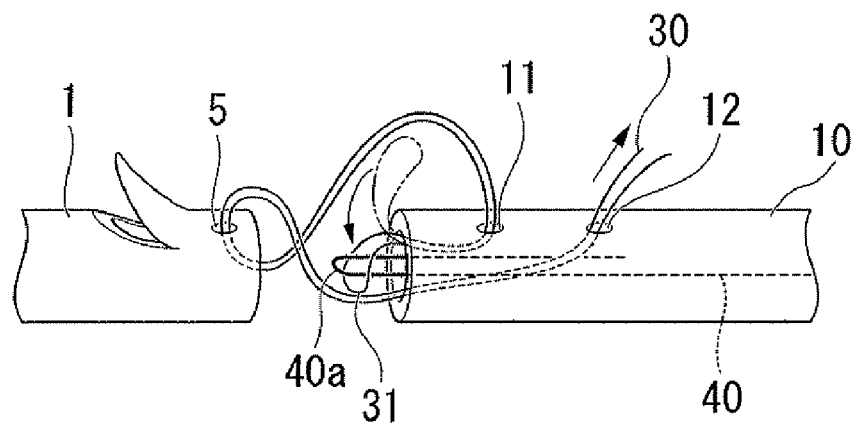
FIG. 6 is a perspective view which shows the connecting method between the stent and the pusher tube by the filament in the stent delivery system of the first embodiment.

Next, as shown in FIG. 6, this protruded loop 31 is arranged at the extended part of the distal end side where the stilet 40 exists, and the stilet moves to the distal end side again, and the distal end portion 40a is passed through the loop 31. That is, the bent distal end portion 40a of the stilet 40 is engaged with the loop 31 in the distal end side of the filament 30. In this condition, the temporary fixture of the filament 30 is removed, and the slack of the filament 30 is removed by pulling the proximal end of the filament 30 in the outer direction.

Figure 7:
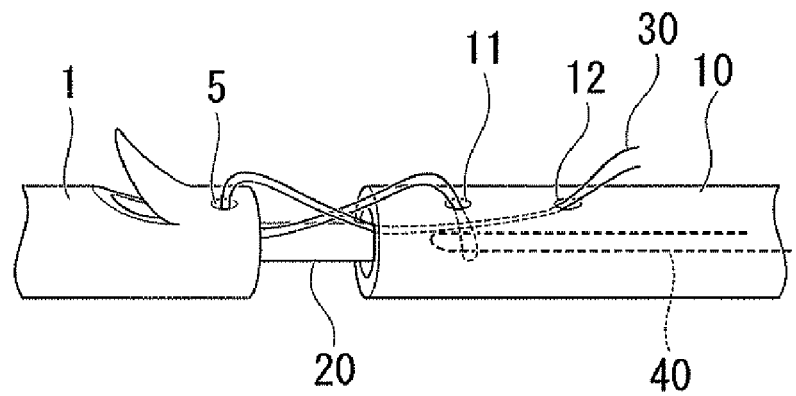
FIG. 7 is a perspective view which shows the connecting method between the stent and the pusher tube by the filament in the stent delivery system of the first embodiment.

Next, as shown in FIG. 7, the stilet 40 is pulled proximally so as to position the distal end of the stilet 40 in the hollow portion of the pusher tube 10. Simultaneously, the guide catheter 20 is passed through the respective hollow portions of the stent 1 and the pusher tube 10.

Next, the stent 1 and the pusher tube 10 are made approach so as not to make a gap between the proximal end of the stent 1 and the distal end of the pusher tube 10. In this condition, the proximal end of the filament 30 is again pulled in the outer direction. Then, the proximal end side of the filament 30 is wrapped around the outer periphery of the pusher tube 10 and is fixed by glue and the like.

Figure 8:
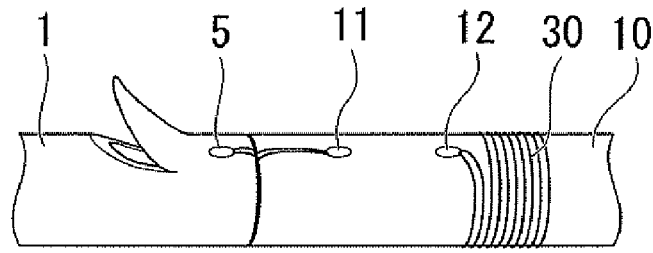
FIG. 8 is a perspective view which shows the connecting method between the stent and the pusher tube by the filament in the stent delivery system of the first embodiment.

With the above, as shown in FIG. 8, the stent 1 and the pusher tube 10 can be connected by the filament 30.

Next, a process of maneuver for disposing the stent in the constricted portion formed to the bile duct by using the stent delivery system S1 constituted like the above shall be described.

Figure 9:
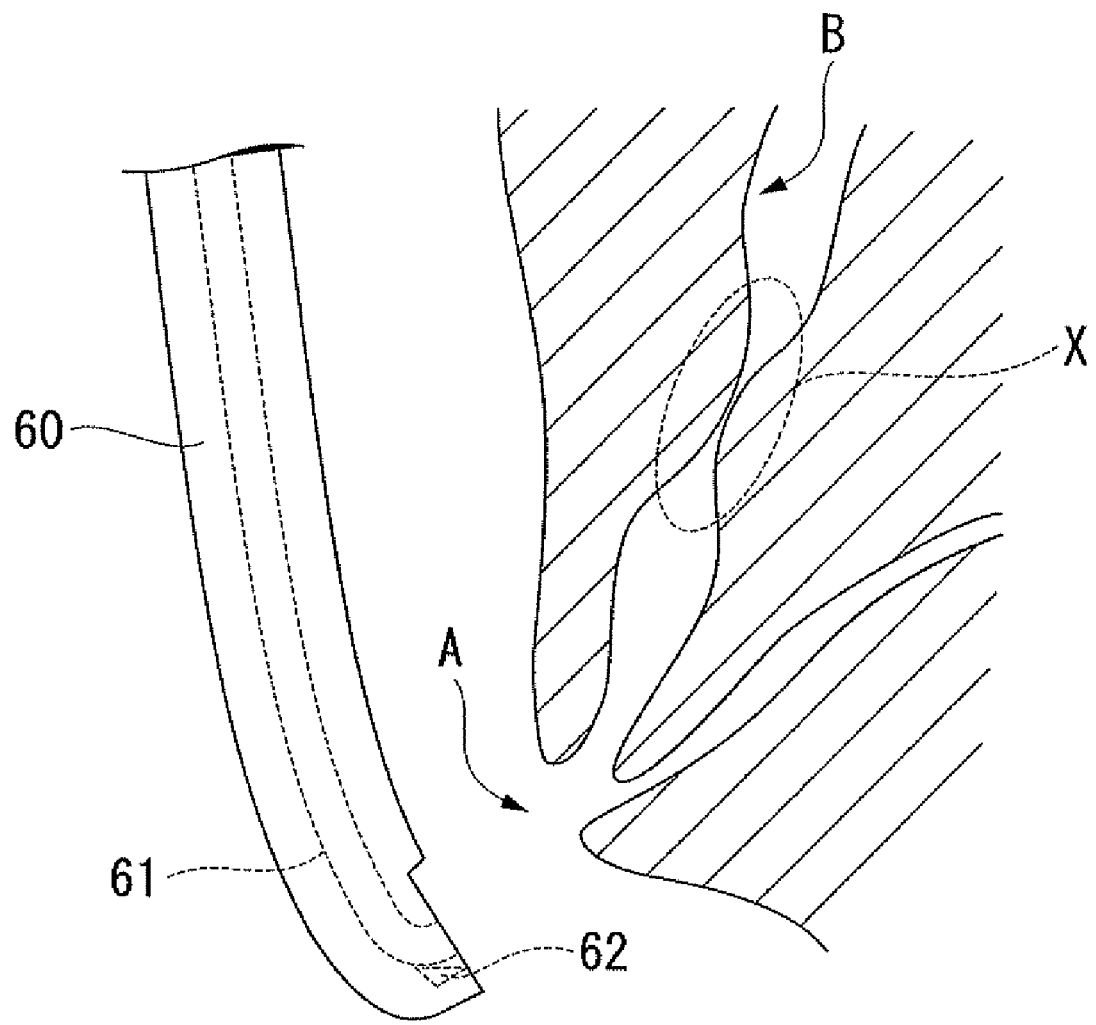
FIG. 9 shows the procedure of the manipulation which is conducted by the stent delivery system of the first embodiment, and shows the condition in which the distal end of the inserting portion of the endoscope is arranged in the vicinity of the duodenal-papilla.

This maneuver begins with, at first, as shown in FIG. 9, inserting the inserting portion 60 of the endoscope in the living body, and reaching the distal end of the inserting portion 60 in the vicinity of the duodenal papilla A.

Figure 10:
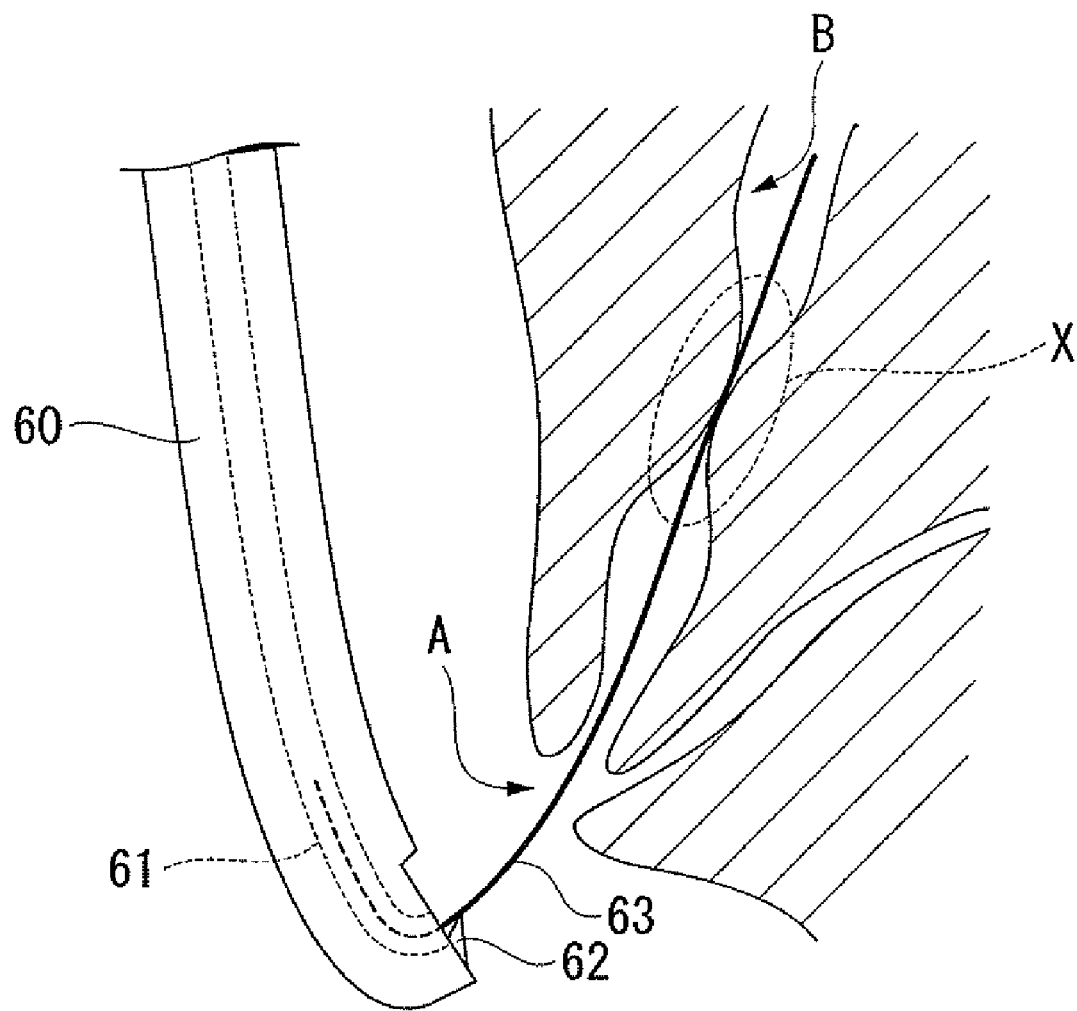
FIG. 10 shows the procedure of the manipulation which is conducted by the stent delivery system of the first embodiment, and shows the condition in which the guidewire is inserted in the constricted portion of the bile duct.

Next, a canula not illustrated is inserted in the channel 61 of the inserting portion 60, and is made protrude from the distal end of the inserting portion 60. In addition, a rising block 62 which is provided in the distal end of the inserting portion 60 makes the canula bent, and the distal end of the canula is inserted in the bile duct B. Then, the contrast medium is injected in the bile duct B through the canula. When the contrast medium has been injected, a guidewire 63 is inserted in the constricted portion X of the bile duct B through the canula, and as shown in FIG. 10, the canula is pulled out of the bile duct B and the channel 61 with remaining only the guidewire 63.

Figure 11:
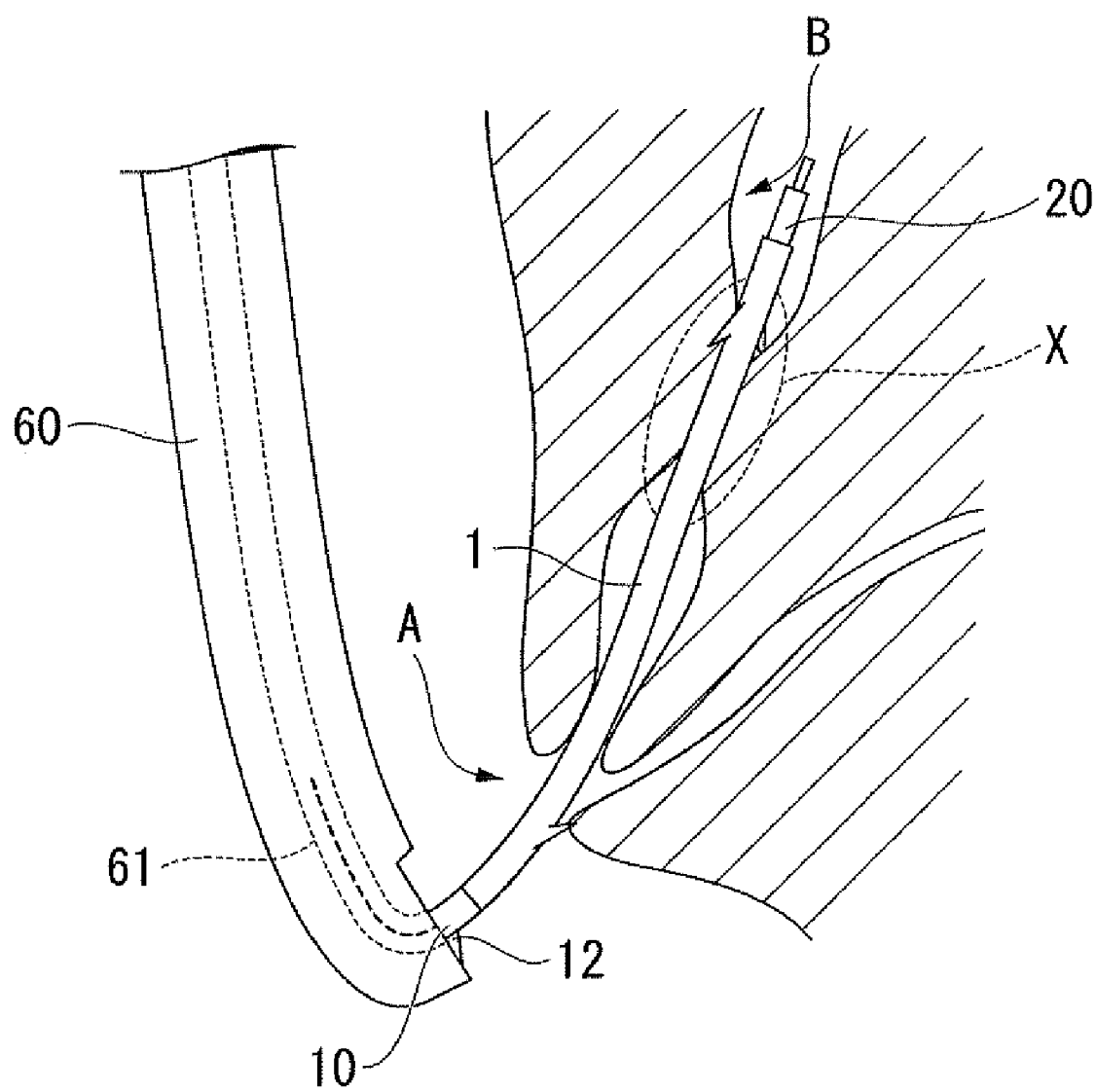
FIG. 11 shows the procedure of the manipulation which is conducted by the stent delivery system of the first embodiment, and shows the condition in which the stent and the guide catheter are inserted in the constricted portion.

Next, five members combined as shown in FIG. 1, i.e. the stent 1, the pusher tube 10, the guide catheter 20, the filament 30, the stilet 40 and the guidewire 50, are inserted into a channel 61 along the guidewire 63, and are protruded from the distal end of the inserting portion 60. In addition, the guide catheter 20 and the pusher tube 10 are bent by the rising block 62, and as shown in FIG. 11, the stent 1 and the guide catheter 20 are inserted in the narrow portion X.

Figure 14:
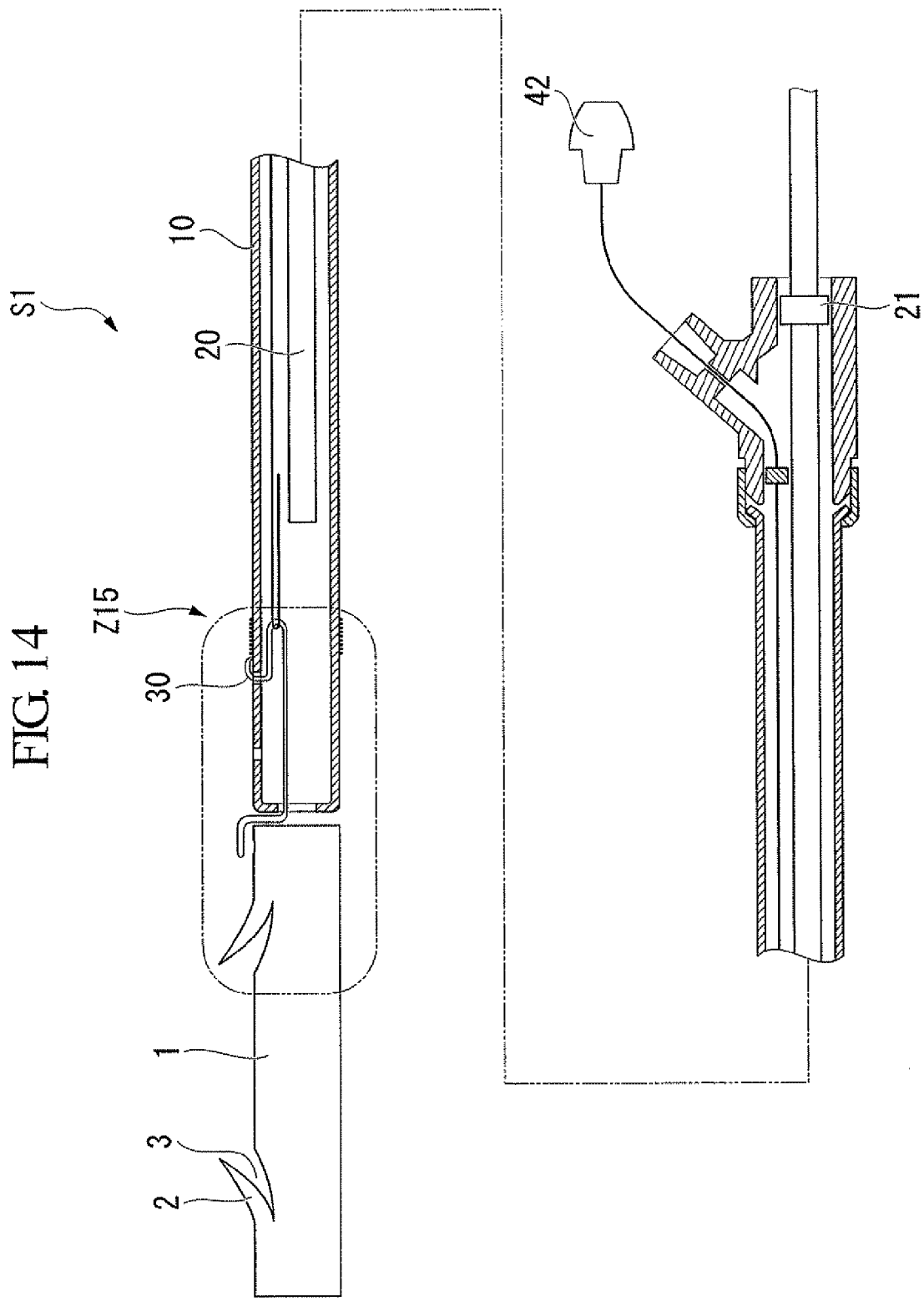
FIG. 14 shows the procedure of the manipulation which is conducted by the stent delivery system of the first embodiment, and shows the condition in which the guide catheter and the stilet have been retreated.
Figure 15:
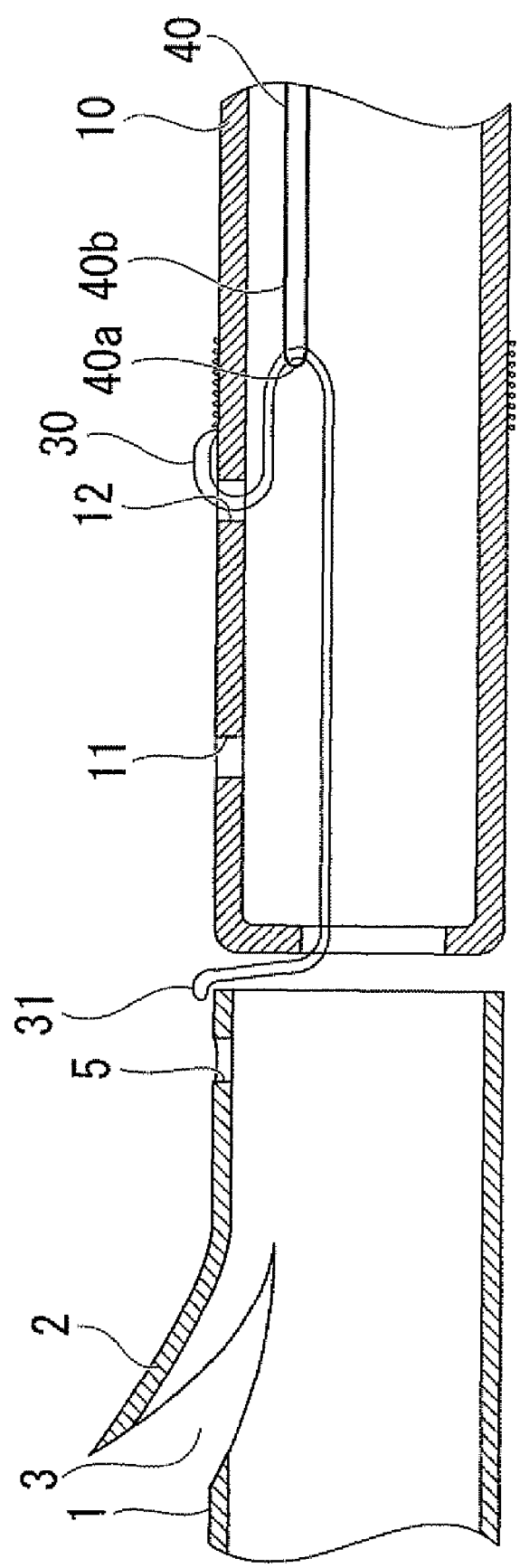
FIG. 15 is an enlarged cross-sectional view of Z15 part in FIG. 14.

Next, as shown in FIG. 14, by gripping the cap 22 and pulling it to the outer direction, the guide catheter 20 is moved proximally, the distal end portion of the guide catheter 20 is pulled out of the hollow portion of the stent 1, and the restriction of the stent by the guide catheter 20 is released. After that, by pulling the cap 42 to the outer direction, the stilet 40 is moved proximally, the distal end portion 40a is pulled out of the loop of the filament, and the connection between the stent 1 and the pusher tube 10 by the filament 30 is released.

Here, the connection between the stent 1 and the pusher tube 10 by the filament 30 cannot be released by moving the stilet 40 proximally before the guide catheter 20 is moved and the restriction of the stent 1 is released by the guide catheter 20.

In short, as shown in FIG. 12, if the cap 42 is gripped and pulled as keeping the guide catheter 20 and the pusher tube 10 in a fixed position, and the stilet 40 is tried to move proximally before the guide catheter 20, it is impossible to move the stilet 40 further proximally since the second stopper 41 is bumped to the first stopper 21.

In this time, the distal end portion 40a of the stilet 40 is, as shown in FIG. 13, positioned in more distal than the first through-hole 11 of the pusher tube 10. Therefore, the distal end portion 40a of the stilet is not pulled out of the loop 31 of the filament 30, and the connection between the stent 1 and the pusher tube 10 by the filament 30 is maintained.

On the other hand, as shown in FIG. 14, if the guide catheter 20 is moved previously proximally and the distal end portion of the guide catheter 20 is pulled out of the hollow portion of the stent 1, it is possible to move the stilet 40 proximally and make the distal end portion 40a reach more proximal than the first and the second through-holes 11, 12 without bumping the second stopper 41 with the first stopper 21 since the first stopper 21 has been moved proximally.

Here, when the stilet 40 is moved proximally, the distal end portion 40a is pulled out of the loop 31 of the filament 30 at the position where the distal end portion 40a is beyond the first through-hole 11. Thereby, the engagement of the loop 31 at the distal end of the filament 30 by the distal end portion 40a is released, and the connection between the stent 1 and the pusher tube 10 by the filament 30 is released.

After that, when the stilet 40 is moved further proximally, the bent fold-over portion 40b of the stilet 40, the distal end portion of which is engaged with a part of the filament 30, pulls the distal end side of the filament in the proximal end side of the pusher tube 10. In the process, the distal end side of the filament 30 is passed through the first through-hole 11 of the pusher tube 10 and the through-hole 5 of the stent in order, finally is pulled in the hollow portion in more proximal than the second through-hole 12 of the pusher tube 10. Therefore, the filament 30 does not twine around the stent 1, and the connection between the stent 1 and the pusher tube 10 is released completely.

Figure 16:
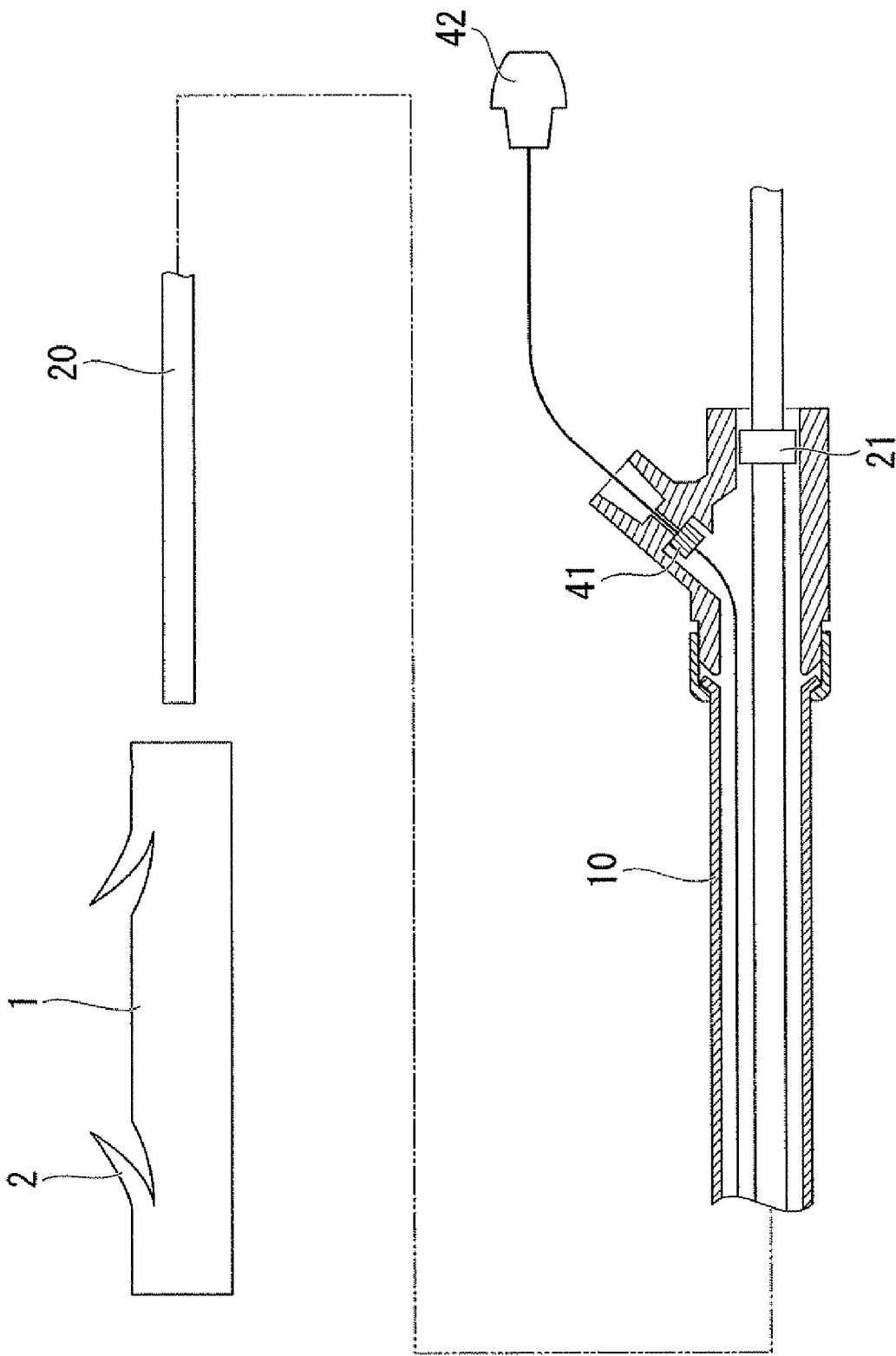
FIG. 16 shows the procedure of the manipulation which is conducted by the stent delivery system of the first embodiment, and shows the condition in which the stent is detained.

Next, as shown in FIG. 16, if the pusher tube 10 is pulled and moved proximally, the pusher tube is going separate from the stent 1 which is fixed in a prescribed position since the connection between the stent 1 and the pusher tube 10 by the filament 30 has been released completely, and as shown in FIG. 16, only the stent 1 is finally detained in the constricted portion X.

According to the stent delivery system S1 constituted like the above, since the distal end side of the filament 30 can be pulled in the pusher tube 10 by moving the stilet 40 proximally, the filament 30, which can move freely after the engagement with the loop 31 of the filament 30 by the distal end portion of the stilet 40 is released, is not twined around the flap 2 of the stent 1 and the like carelessly when the pusher tube 10 is moved proximally. Therefore, it is possible to avoid the stent 1, of which the connection with the pusher tube 10 has been released, from being in the connecting condition or the semi-connecting condition with the pusher tube 10 by the filament 30 again. In addition, it is also possible to prevent the filament 30, the engagement of which with the distal end portion 40a of the stilet 40 has been released, from being in the condition to be entangled with the stent 1, and also to prevent the stent 1 from being moved proximally together with the pusher tube 10 which moves proximally. These results enable the stent 1 to be detained in the constricted portion X accurately.

Additionally, in this embodiment, the engagement of the distal end portion 40a of the stilet 40 with the loop 31 of the filament 30 functions so that the connecting condition between the stent 1 and the pusher tube 10 by the filament 30 can be maintained, and the bent fold-over portion 40b in the distal end side functions so as to pull the distal end side of the filament 30, the connection of which with the stent 1 and the pusher tube 10 has been released, proximally of the pusher tube 10. In short, since the stilet 40 which is a single member has two functions which are the engaging function engaged by the filament 30 and the pulling function to pull the filament 30 proximally, the reduction of the number of parts and the simplification of the constitution can be achieved compared with the case constituted by the separate parts.

In addition, when the stent delivery system S1 is inserted into a prescribed position in a living body along the channel 61 of the endoscope after the stent delivery system S1 is set, taking the stilet 40 being situated deviated from the center of the pusher tube 10 into account since the tissue in a living body has a plurality of the bent portions, there is a possibility that the relative position of the distal end portion 40a of the stilet 40 to the distal end position of the pusher tube 10 is deviated in the axial direction and the distal end portion of the stilet 40 is pulled out of the loop 31 of the filament 30. However, in this embodiment, since the length of the stilet 40 is set longer than the length of the pusher tube 10 and the distal end portion 40a of the stilet 40 is bumped against the wall portion 13a of the narrow portion 13 of the pusher tube 10 by the elasticity of the stilet itself, the distal end portion of the stilet 40 is not pulled out of the loop 31 of the filament 30 even if the position of the distal end portion 40a of the stilet 40 relative to the distal end of the pusher tube 10 is slightly deviated in the axial direction. In short, in this embodiment, when the stent delivery system S1 is inserted into a prescribed position in a living body after being set, the distal end portion 40a of the stilet 40 is not pulled out of the loop 31 of the filament 30 carelessly, and the connection between the stent 1 and the pusher tube 1O by the filament 30 is maintained as far as the stilet 40 is not manipulated to move proximally via the cap 42 after moving the guide catheter 20 proximally.

Moreover, since the gap C between the inner end of the narrow portion 13 of the pusher tube 10 and the outer peripheral surface of the guide catheter 20 is set in a value which is larger than the outer diameter of the filament 30 and smaller than the outer diameter of the stilet 40, the distal end portion 40a of the stilet 40 is not protruded from the gap C to the outer direction of the pusher tube. Then, there is no possibility that the distal end portion 40a of the stilet 40 damages the tissue in a body cavity or the stent 1 by the protrusion out of the pusher tube 10.

Moreover, since the second stopper 41 attached to the stilet 40 is situated in a prescribed position which is more distal than the first stopper 21 attached to the guide catheter 20, the engagement with the distal end portion of the stilet 40 relative to the loop 31 of the filament 30 cannot be released as far as the guide catheter is not moved proximally more than the prescribed value. In short, as far as the guide catheter 20 is not pulled out of the hollow portion of the stent 1, the connection between the stent 1 and the pusher tube 10 cannot be released. Thereby, not after the stent 1 is set in a accurate position by the guide catheter 20, the connection between the stent 1 and the pusher tube 10 cannot be released. In this point, the stent 1 can be detained in more accurate position. In addition, if it is in a case that the position of the stent 1 is deviated when the guide catheter 20 is pulled out of the stent 1, it is possible to adjust the position of the stent 1 via the pusher tube 10 since the stent 1 and the pusher tube 10 are connected.

Moreover, when the stent 1 is fixed to the pusher tube 10 via the filament 30, since the filament 30 is passed through two through-holes 11, 12 provided with the pusher tube 10, the workability when the filament 30 is passed through can be improved and it is easy to judge after connection whether the connection is well conducted or not compared with the case that only one through-hole is provided with the pusher tube 10.

Furthermore, when the filament 30 is engaged with the stent 1, since the filament is wrapped around between the proximal end of the stent 1 and the through-hole 5 so as to form a circumference, it is possible to restrict the area where the loop 31 which is the distal end of the filament 30 can move freely when the engagement with the distal end portion 40a of the stilet 40 is released and the filament 30 is pulled out of the through-holes 11, 5 and loosened. Thereby, it is possible to prevent the filament 30 from being twined with the flap 2 of the stent 1 or the like inadvertently.

Second Embodiment

A second embodiment of the stent delivery system of the present invention shall be described with reference to FIGS. 17 to 29.

Figure 17:
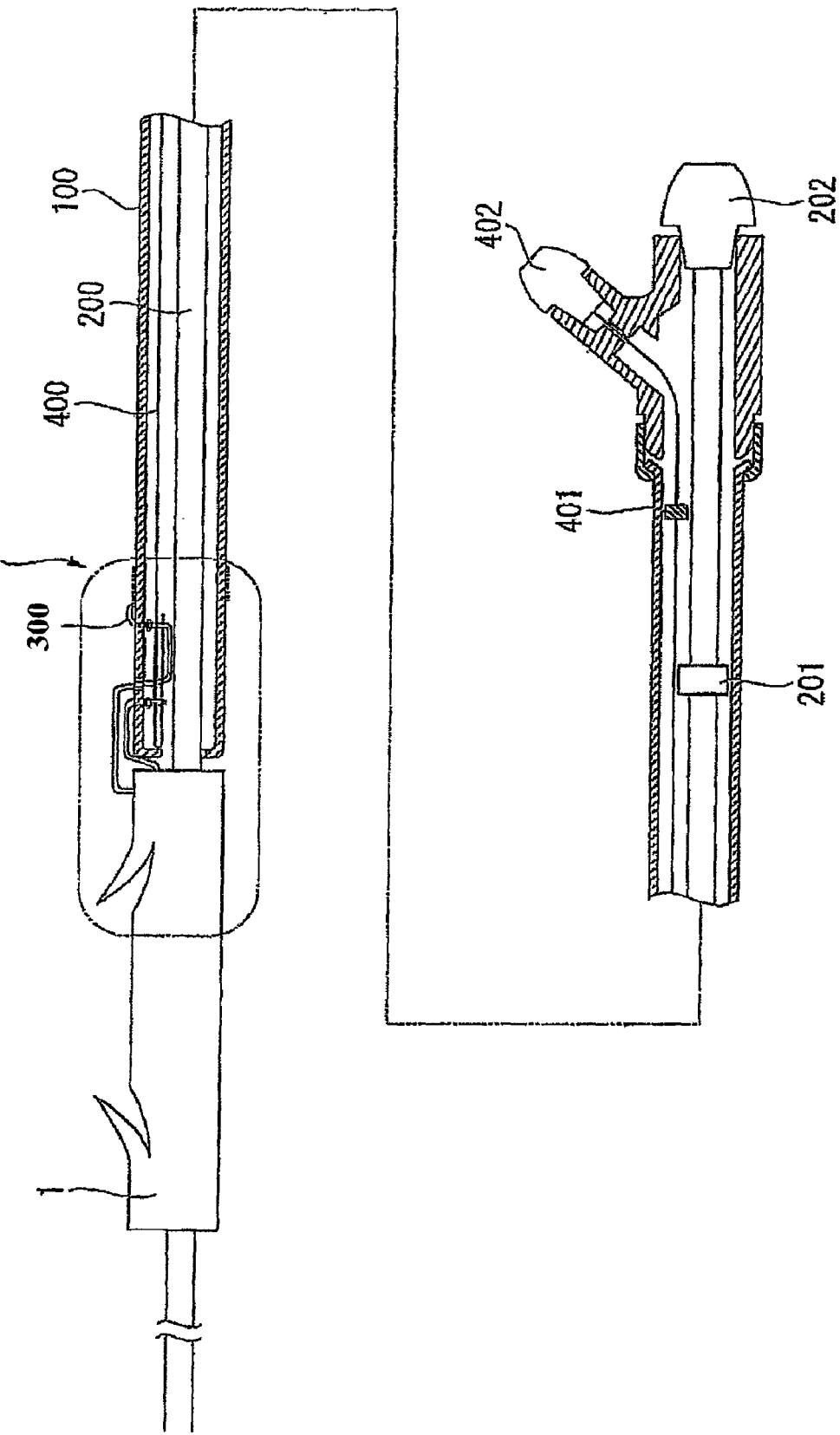
FIG. 17 is a partial cross-sectional view which shows a second embodiment of the stent delivery system of the present invention.

The stent delivery system S2 in this embodiment is provided with a stent 1, a pusher tube 100, a guide catheter 200, a filament 300, and a stilet 400 as shown FIG. 17.

Figure 18:
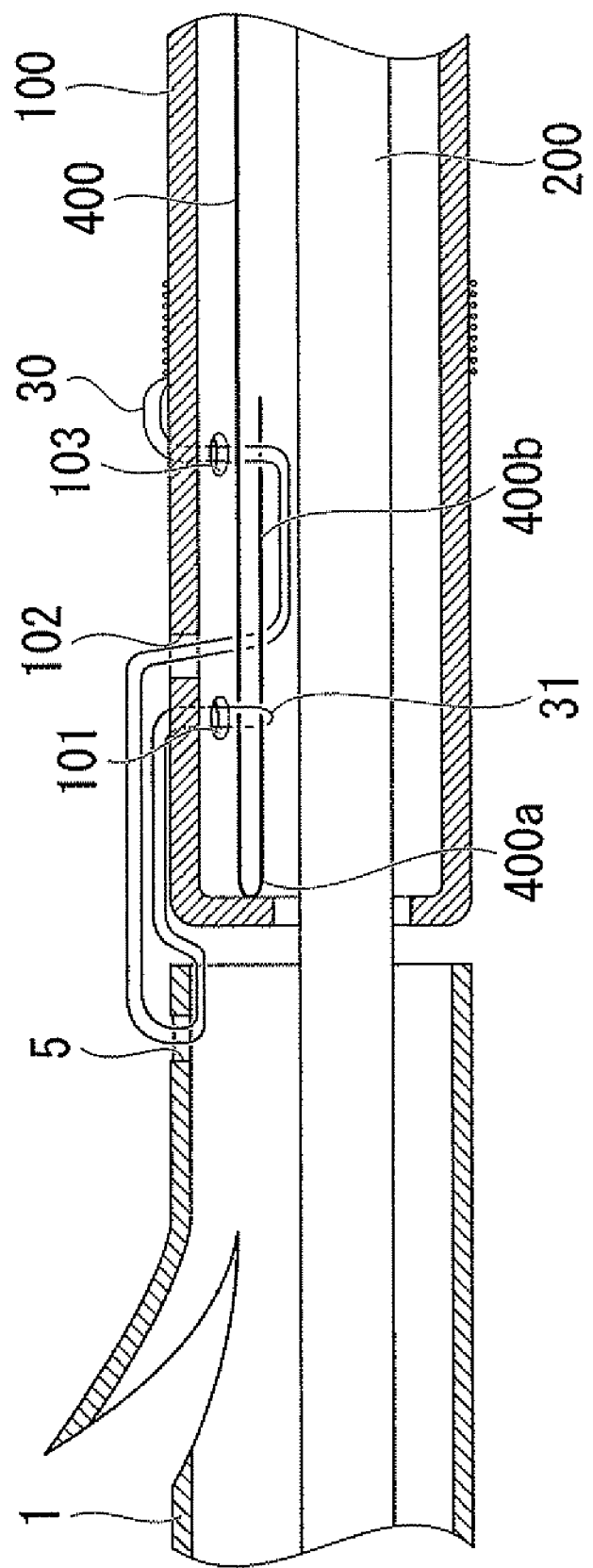
FIG. 18 is an enlarged cross-sectional view of Z18 part in FIG. 17.

The pusher tube 100 is made of resin, and is formed flexible, elongate, and tubular. As shown in FIG. 18, three through-holes (the first, the second, and the third through-holes) 101, 102, 103 which are used to pass the filament through, are formed at the distal end portion of the pusher tube 100. The first through-hole 101 and the second through-hole 102 are formed at more proximally than the bent area of the pusher tube 100 when the pusher tube 100 is projected from the distal end of the inserting portion 60 of the endoscope in the procedure. The first and the third through-holes 101, 103 are formed so as to be parallel to the axis of the pusher tube 100, and the second through-hole 102 is formed at a position deviated in the peripheral direction relative to the first and the third through-holes 101, 103. In addition, the first through-hole 101 and the second through-hole 102 are formed at a position which is in slightly more proximal end side from the distal end of the pusher tube 100, and the third through-hole 103 is formed at a position which is further more proximal end side than the position of the first and the second through-holes 101, 102.

The guide catheter 200 is a flexible-resin-made elongate and tubular component similarly to the pusher tube 100. The first stopper 201 is attached to the outer periphery of the distal end of the guide catheter 200 which is covered by the pusher tube 100 when it is set in the channel of the inserting portion. The size of the first stopper 201 is set to be greater than the outer diameter of the guide catheter 200 and smaller than the inner diameter of the pusher tube 100. In addition, a cap 202, which is gripped by an operator when the guide catheter 200 is operated, is provided at the proximal end of the guide catheter 200.

On the other hand, the freely extendable and retractable stilet 400 is constituted of a linear member, for example, a wire made of resin or metal, and is arranged between the inner peripheral surface of the pusher tube 100 and the outer peripheral surface of the guide catheter 200 inserted in the inner hollow portion of the pusher tube 100 so as to be moved independently with the guide catheter 200 along the axial direction. A second stopper 401 is attached at the portion which is the outer periphery of the proximal end of the stilet 400 and is covered with the pusher tube 100 when the stilet 400 is attached to a channel of the inserting portion. The size of the second stopper 401 is set to be greater than the outer diameter of the stilet 400 and smaller than the inner diameter of the pusher tube 100.

In addition, the first stopper 201 is arranged more distally relative to the second stopper 401 on the hollow portion of the pusher tube 100. In addition, the second stopper 401 is arranged more distally of the hollow portion of the pusher tube 100 than the first stopper 201 which is attached to the guide catheter 200. In short, the first stopper 201 and the second stopper 401 are in the interfering relation each other in the inner hollow portion of the pusher tube 100. When the guide catheter 200 is moved proximally before the stilet 400, it can be moved in a distance. However, when the guide catheter 200 is tried to move more, it cannot be moved since the first stopper is bumped to the second stopper 401. But after the stilet 400 is moved proximally, the guide catheter 200 can be moved proximally since the second stopper 401 is moved proximally.

Figure 25:
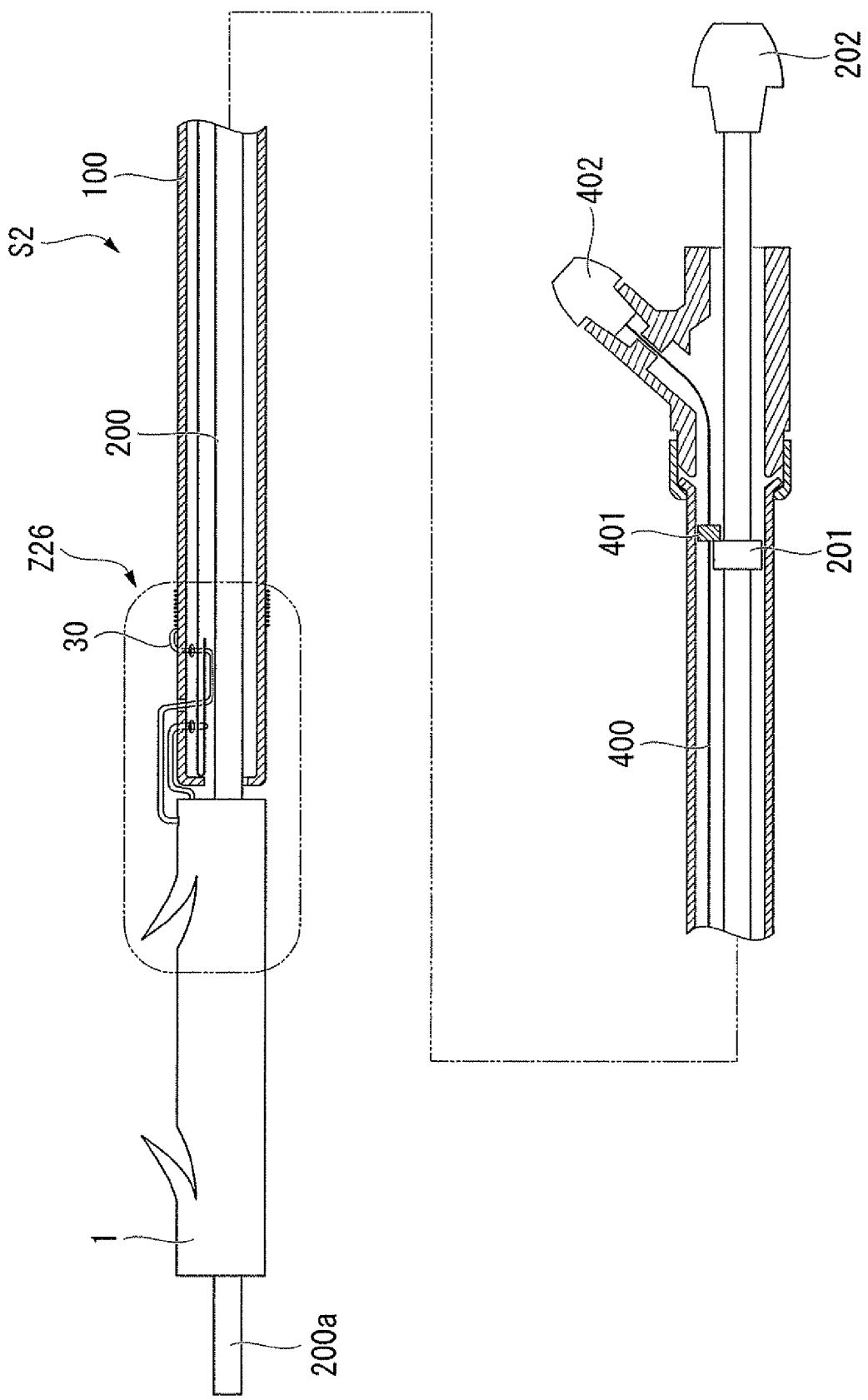
FIG. 25 shows the procedure of the manipulation which is conducted by the stent delivery system of the second embodiment, and shows the condition in which the stilet is going to be retreated at first.
Figure 26:
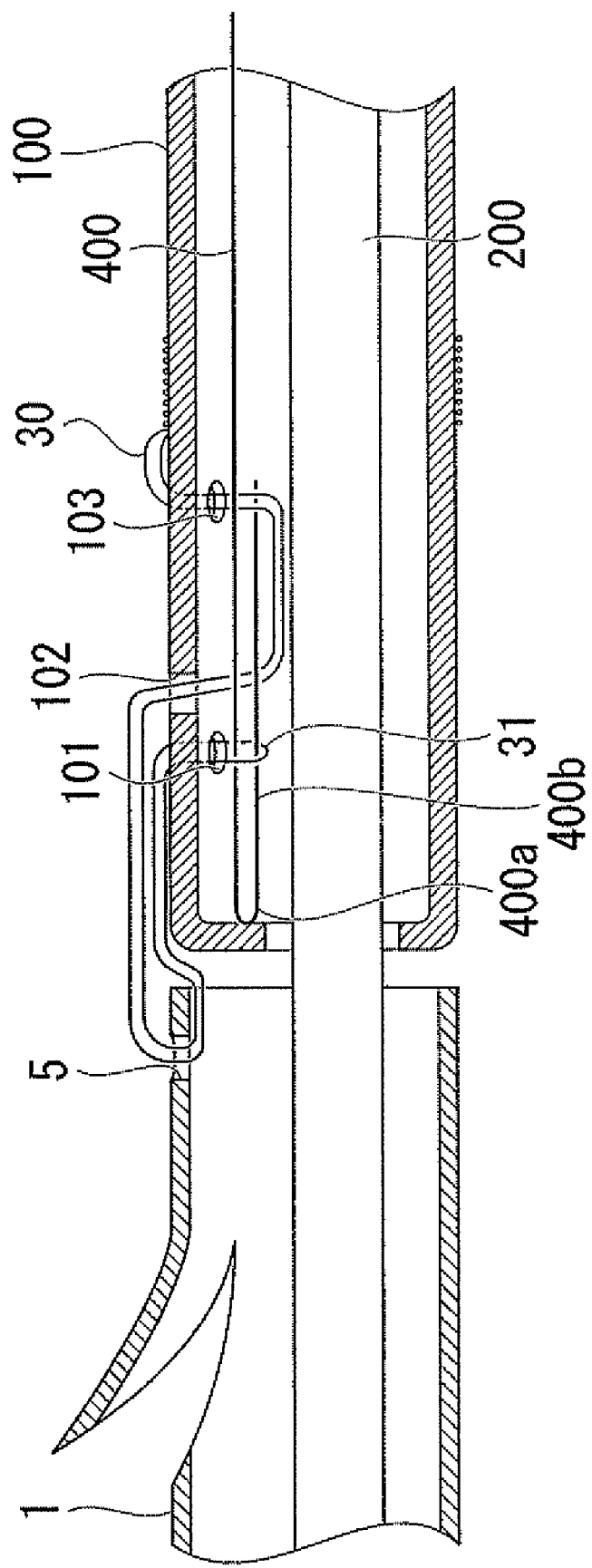
FIG. 26 is an enlarged cross-sectional view of Z26 part in FIG. 25.

The relative position at the first stopper 201 and the second stopper 401 as shown in FIG. 25, FIG. 26, is set so that the distal end portion 200a of the guide catheter 200 is positioned in more distal than the distal end of the stent 1 and the restriction of the stent 1 by the guide catheter 200 is maintained when the guide catheter 200 is moved proximally before the stilet 400 and is in the condition that the first stopper 201 is bumped to the second stopper 401.

In addition, the proximal end of the stilet 400 is provided with the cap 402 which is gripped by the operator when the stilet 400 is manipulated to retreat.

Next, the connecting method between the stent 1 and the pusher tube 100 by using the filament 30 in this embodiment shall be described with reference to FIG. 19 to FIG. 24.

Figure 19:
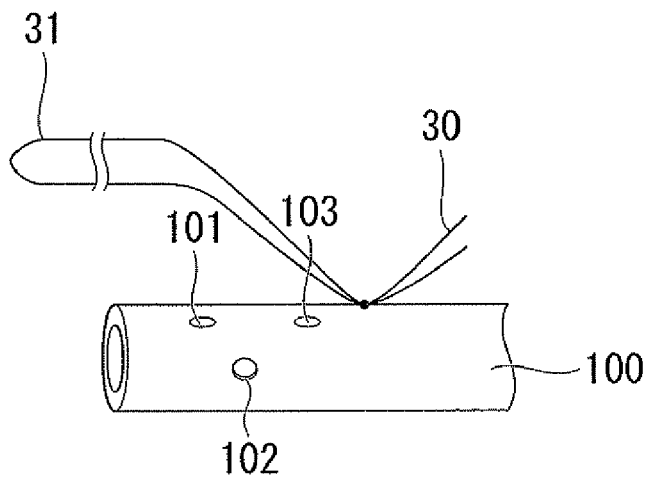
FIG. 19 is a perspective view which shows the connecting method between the stent and the pusher tube by the filament in the stent delivery system of the second embodiment.

As shown in FIG. 19, first, in a prescribed portion in the proximal end side of the filament 30 is fixed temporarily to the portion which is outer periphery of the pusher tube 100 and is in the vicinity of the third through-hole 103 by such a suitable fixing means as glue or the like. The more distal end side of the filament 30 than the portion fixed temporarily is passed through the second through-hole 103 so as to be directed from the outer peripheral surface to the inner peripheral surface, and is made protruded to the outer direction out of the opening of the distal end side through the hollow portion of the pusher tube 100.

Figure 20:
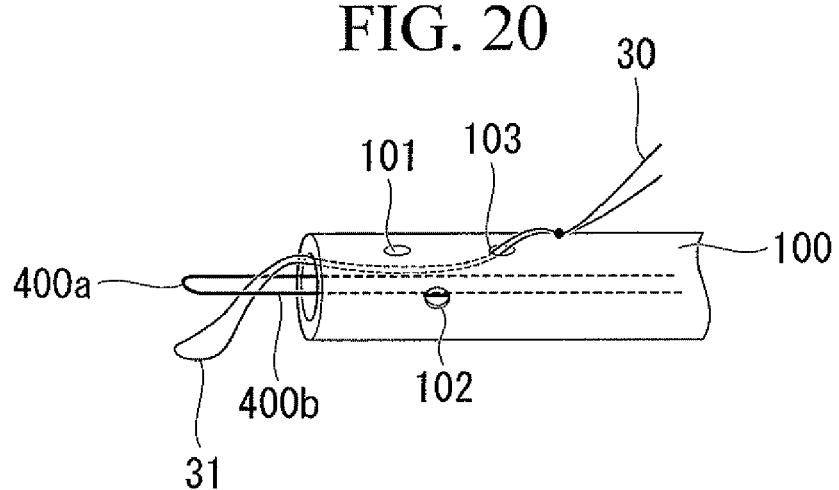
FIG. 20 is a perspective view which shows the connecting method between the stent and the pusher tube by the filament in the stent delivery system of the second embodiment.

Next, as shown in FIG. 20, the bent distal end portion 400a of the stilet 400 to have been made insert beforehand is made protrude to the outer direction out of the opening of the distal end side of the pusher tube 100. The loop 31 of the filament 30 is passed through the bent fold-over portion 400b of the stilet 400 which is made protrude.

Figure 21:
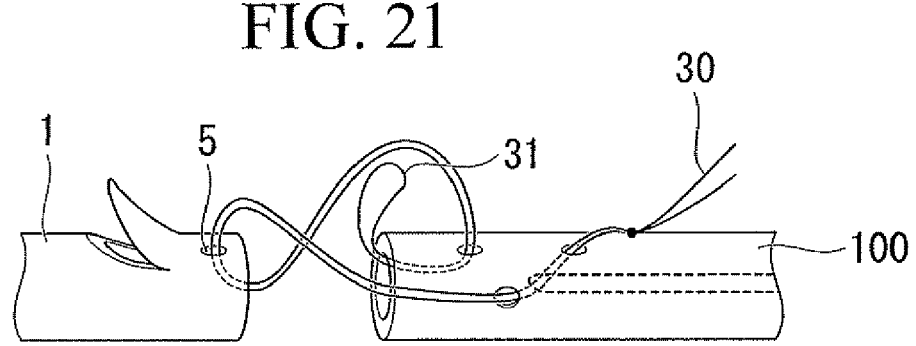
FIG. 21 is a perspective view which shows the connecting method between the stent and the pusher tube by the filament in the stent delivery system of the second embodiment.

Next, as shown in FIG. 21, the stilet 400 is pulled in the proximal end side and the distal end portion 400a is returned in the hollow portion of the pusher tube 100. Concurrently with this operation, the loop 31 of the filament 30 is passed through the second through-hole 102 of the pusher tube 100 so as to be directed from the outer peripheral surface to the inner peripheral surface, and after that, the loop 31 is bent proximally and is pulled out from the opening of the proximal end side of the stent 1 to the outer direction. In this time, the filament 30 is wrapped around between the proximal end of the stent 1 and the through-hole 5 formed in the peripheral wall so as to form a circumference. Additionally, the loop 31 which has been pulled out is passed through the first through-hole 100 of the pusher tube 101 so as to be directed from the outer peripheral surface to the inner peripheral surface. The loop 31 after being passed through the first through-hole 101 is bent to the distal end side of the pusher tube 100, and is made protruded to the outer direction out of the opening of the distal end side.

Figure 22:
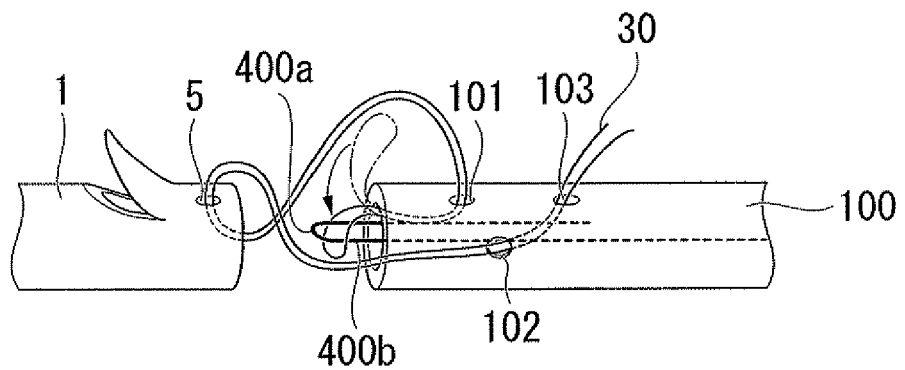
FIG. 22 is a perspective view which shows the connecting method between the stent and the pusher tube by the filament in the stent delivery system of the second embodiment.

Next, as shown in FIG. 22, the protruded loop 31 is arranged at the extended part of the distal end side where the stilet 400 exists, and the stilet moves to the distal end side again, and the distal end portion 400a is passed through the loop 31. That is, the bent distal end portion 400a of the stilet 400 is engaged with the loop 31 in the distal end side of the filament 30. In this condition, the temporary fixture of the filament 30 is removed, and the slack of the filament 30 is removed by pulling the proximal end of the filament 30 in the outer direction.

Figure 23:
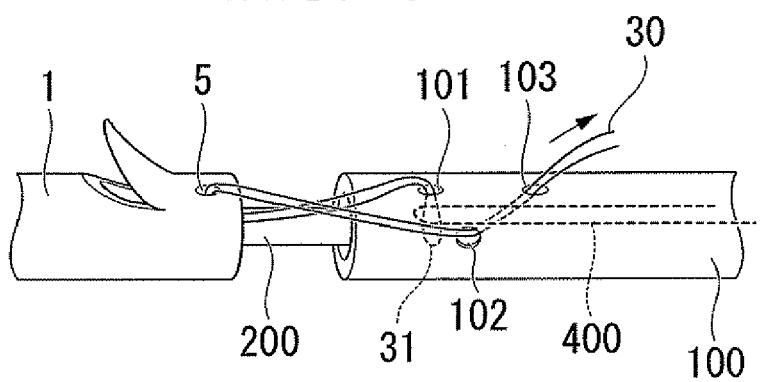
FIG. 23 is a perspective view which shows the connecting method between the stent and the pusher tube by the filament in the stent delivery system of the second embodiment.

Next, as shown in FIG. 23, the stilet 400 is pulled proximally so as to position the distal end of the stilet 400 in the hollow portion of the pusher tube 100. Simultaneously, the guide catheter 200 is passed through the respective hollow portions of the stent 1 and the pusher tube 100.

Next, the stent 1 and the pusher tube 100 are made approach so as not to make a gap between the proximal end of the stent 1 and the distal end of the pusher tube 100. In this condition, the proximal end side of the filament 30 is again pulled in the outer direction. Then, the proximal end side of the filament 30 is wrapped around the outer periphery of the pusher tube 100 and is fixed by glue.

Figure 24:
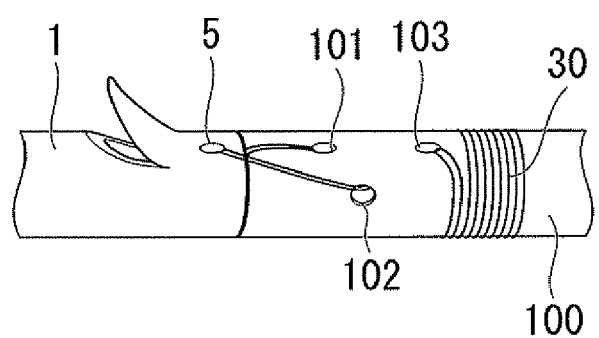
FIG. 24 is a perspective view which shows the connecting method between the stent and the pusher tube by the filament in the stent delivery system of the second embodiment.

With the above, as shown in FIG. 24, the stent 1 and the pusher tube 100 can be connected by the filament 30.

Next, a process of maneuver for disposing the stent in the constricted portion formed to the bile duct by using the stent delivery system S1 constituted like the above shall be described.

In the maneuver, the procedure till the guidewire is set in a prescribed position by using the endoscope in a living body is the same as that of the first embodiment described above.

Next, five members combined as shown in FIG. 17, i.e. the stent 1, the pusher tube 100, the guide catheter 200, the filament 30, and the stilet 400, are inserted into a channel along the guidewire, and are protruded from the distal end of the inserting portion. In addition, the guide catheter 200 and the pusher tube 100 are bent by the rising block, and as shown in FIG. 11, the stent 1 and the guide catheter 200 are inserted in the narrow portion X.

Figure 27:
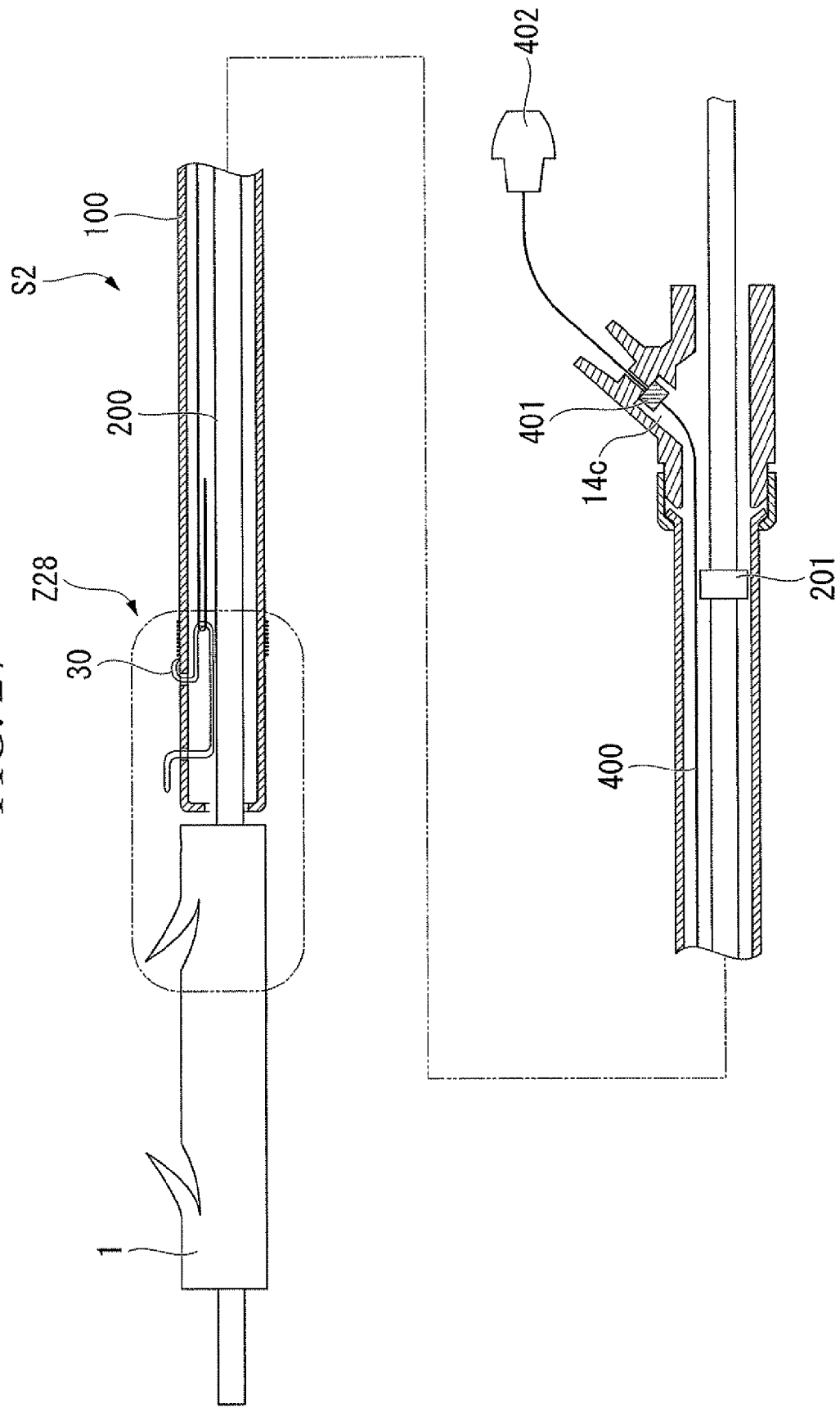
FIG. 27 shows the procedure of the manipulation which is conducted by the stent delivery system of the first embodiment, and shows the condition in which the guide catheter and the stilet have been retreated.
Figure 28:
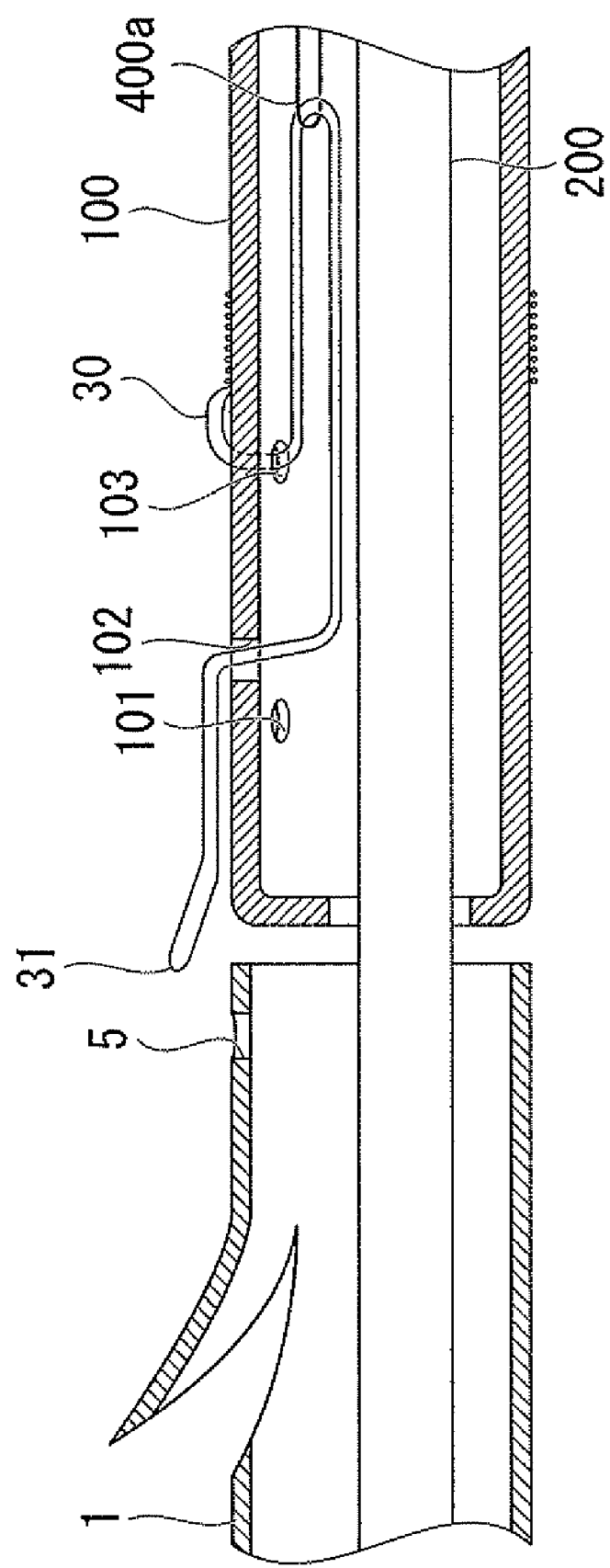
FIG. 28 is an enlarged cross-sectional view of Z28 part in FIG. 27.

Next, as shown in FIG. 27, by gripping the cap 402 and pulling it to the outer direction, the stilet 400 is moved proximally before the guide catheter 200, the distal end portion 400a of stilet 400 is pulled out of the loop 31 of the filament 30, the connection between the stent 1 and the pusher tube 100 by the filament 30, and the filament, the restriction of which has been released, is pulled in the proximal end side of the pusher tube. After that, by pulling the cap 202 to the outer direction, the guide catheter 200 is moved proximally, the distal end portion of the guide catheter 200 is pulled out of the hollow portion of the stent 1, and the restriction of the stent 1 by the guide catheter 200 is solved.

Here, the restriction of the stent 1 by the guide catheter 200 cannot be solved by moving the guide catheter 200 proximally before the engagement of the filament 30 by the stilet 400 is released and the distal end side of the filament 30 is pulled in by moving the stilet 400.

In short, as shown in FIG. 25, if the cap 202 is gripped and pulled as keeping the guide catheter 200 and the pusher tube 100 in a fixed position, and the guide catheter 200 is tried to move proximally, it is impossible to move the guide catheter 200 further proximally since the first stopper 201 is bumped to the second stopper 401.

In this time, the distal end portion 200a of the guide catheter 200 is, situated in more distal than the distal end of the stent 1, and the restriction of the stent 1 by the guide catheter 200 is not solved.

On the other hand, as shown in FIG. 27, if first, the stilet 400 is moved and made reach more proximal than the distal end portion 400a of the stilet 400 and the third through-hole 103, it is possible to move the guide catheter 200 proximally and pull the distal end of the guide catheter 200 out of the hollow portion of the stent 1 without bumping the first stopper 201 with the second stopper 401 since the second stopper 401 has been stored in the vacant portion 14c.

When the stilet 400 is moved proximally, the distal end portion 400a is pulled out of the loop 31 of the filament 30 at the position where the distal end portion 400a is beyond the first through-hole 101. Thereby, the engagement of the loop 31 at the distal end of the filament 30 by the distal end portion 400a is released, and the connection between the stent 1 and the pusher tube 100 by the filament 30 is released.

After that, when the stilet 400 is moved further proximally, the bent fold-over portion 400b of the stilet 400, the distal end portion of which is engaged with a part of the filament 30, pulls the distal end side of the filament 30 in the proximal end side of the pusher tube 100. In the process, the distal end side of the filament 30 is passed through the first through-hole 101 of the pusher tube 1100, the through-hole 5 of the stent and the second through-hole 102 of the pusher tube 1100 in order, and finally is pulled in more proximal than the second through-hole 102 of the pusher tube 10. Therefore, the filament 30 does not twine around the stent 1, and the connection between the stent 1 and the pusher tube 100 is released completely.

Figure 29:
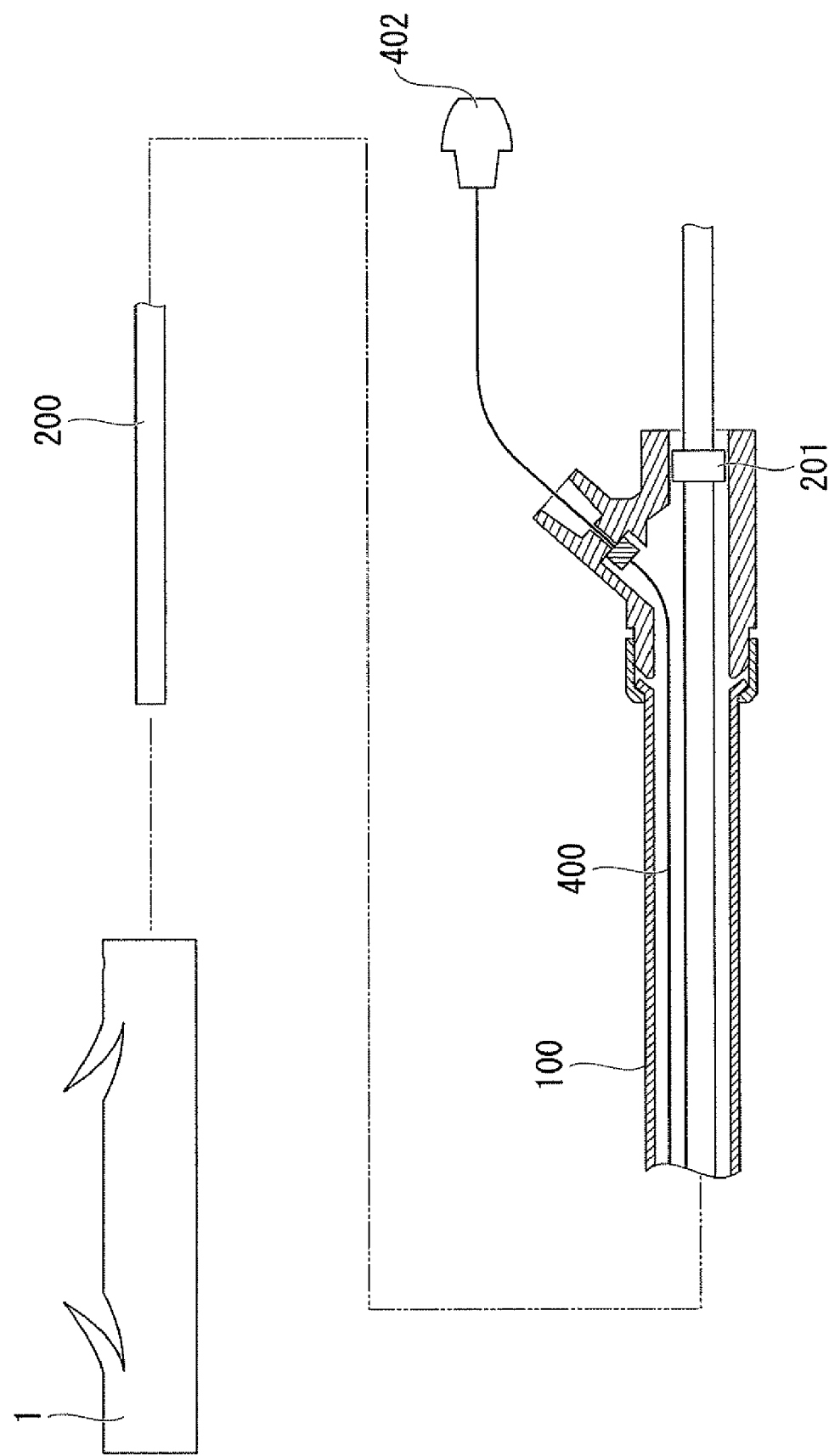
FIG. 29 shows the procedure of the manipulation which is conducted by the stent delivery system of the second embodiment, and shows the condition in which the stent is detained.

Next, as shown in FIG. 29, the guide catheter 200 is moved proximally and the distal end portion of the stent 1 is pulled out of the hollow portion of the stent 1 by gripping the cap 202 and pulling it in the outer direction. That is, the restriction to the stent 1 by the guide catheter 200 is released.

After that, if the pusher tube 100 is pulled and moved proximally, the pusher tube 100 is going separate from the stent 1 which is fixed in a prescribed position since the connection between the stent 1 and the pusher tube 100 by the filament 30 has been released completely, and only the stent 1 is finally detained in the constricted portion X.

In this second embodiment, since the first stopper 201 attached to the guide catheter 200 is situated in a prescribed position which is more distal than the second stopper 401 attached to the stilet 400, the restriction of the stent 1 by the guide catheter 200 cannot be solved as far as the stilet 400 is not moved more proximal than the prescribed value. In short, as far as the connection between the stent 1 and the pusher tube 100 is not released, the restriction of the stent 1 by the guide catheter 200 cannot be solved. Thereby, also after the connection between the stent 1 and the pusher tube 100 is released, it is possible to restrict the stent 1 by the guide catheter 200 so as to be coaxial and to prevent the stent 1 from being deviated to the side direction carelessly.

Moreover, when the stent 1 is fixed to the pusher tube 100 via the filament 30, since the filament 30 is passed through three through-holes 101, 102, 103 provided with the pusher tube 1100, the workability when the filament 30 is passed through can be more improved and it becomes easy to judge after connection whether the connection is well conducted or not compared with the case that one or two through-holes are provided with the pusher tube 100.

Third Embodiment

Figure 30:
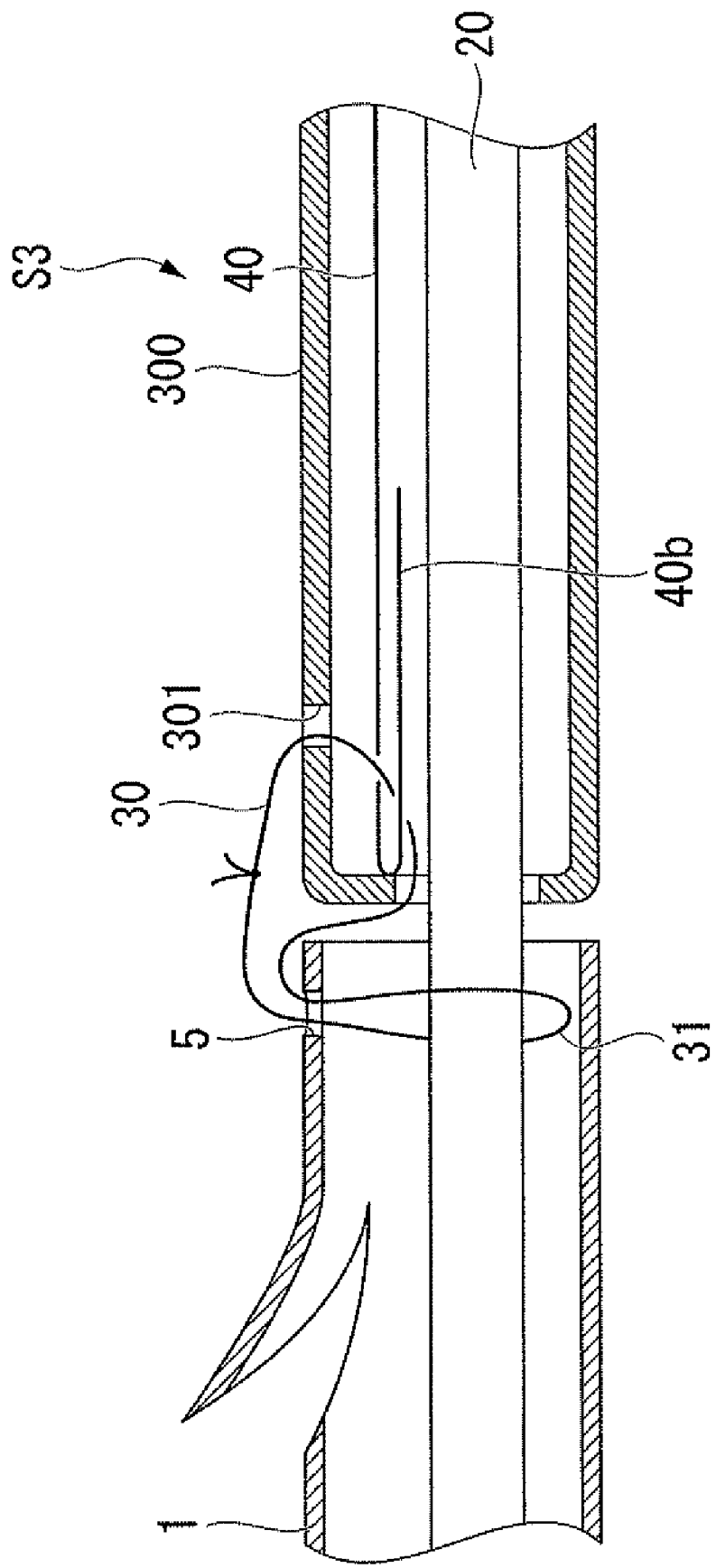
FIG. 30 is a cross-sectional view of the main portion which shows the third embodiment of the stent delivery system of the present invention.

The third embodiment of the stent delivery system of the present invention shall be described with reference to FIG. 30.

The difference point of the stent delivery system S3 of the present embodiment with the stent delivery system S1 of the first embodiment described above is that the filament is simpler wrapped around one through-hole 301 which is provided with pusher tube 300, and that the guide catheter 20 is used as the engaging member which is engaged with the loop 31 of the distal end of the filament 30 keeps the connecting condition between the stent 1 and the pusher tube 300 by the filament 30.

In short, only one through-hole 301 is provided with the pusher tube 300, and the filament 30 is situated between this through-hole 301 and the through-hole 5 of the stent 1 in the condition that the both ends of the filament 30 are tied. The loop 31 is formed at the distal end of the filament 30, and this loop 31 is passed through the through-hole 5 of the stent 1 so as to be directed from the outer peripheral surface to the inner peripheral surface. Additionally, the freely insertable and removable guide catheter 20 is inserted in this loop 31. Moreover, a part of the filament 30 is engaged with the fold-over portion 40b of the stilet 40, the distal end of which is bent to form a U-letter shape.

According to the stent delivery system S3 of the present embodiment, when the guide catheter 20 is moved proximally, this guide catheter 20 is pulled out of the hollow portion of the stent 1 and the engagement with the filament 30 is solved by the guide catheter 20 passed through the loop 31. Thereby, the restriction of the stent 1 by the guide catheter 20 is solved, and the connection is with the pusher tube by the filament 30 is also released.

By moving the stilet 40 proximally after that, the distal end side of the filament 30, the connection of which between the stent 1 and the pusher tube 300 has been released, can be pulled proximally of the pusher tube 300.

Fourth Embodiment

Figure 31:
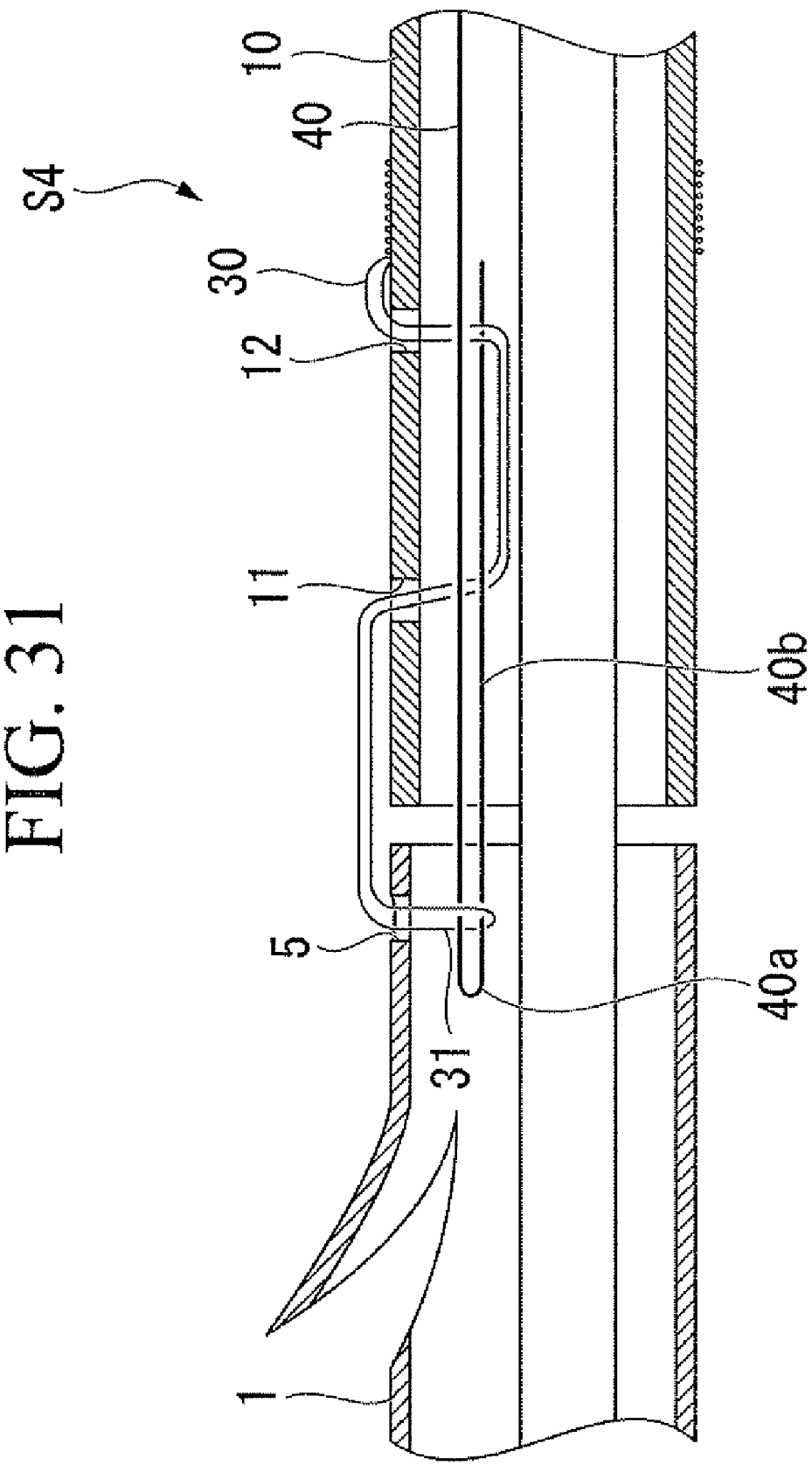
FIG. 31 is a cross-sectional view of the main portion which shows a fourth embodiment of the stent delivery system of the present invention.

A fourth embodiment of the stent delivery system of the present invention shall be described with reference to FIG. 31.

The difference points of the stent delivery system S4 of the present embodiment with the stent delivery system S1 of the first embodiment described above are the way how the filament 30 which connects the stent 1 with the pusher tube 10 is passed through, and that the distal end portion 40a of the stilet 40 is extended to the hollow portion of the stent 1.

In short, the loop 31 at the distal end of the filament 30 is passed through the second through-hole 12 of the pusher tube 10 so as to be directed from the outer peripheral surface to the inner peripheral surface, and after that, it is passed through the first through-hole 11 which is formed at the side which is more distal than the second through-hole 12 so as to be directed from the outer peripheral surface to the inner peripheral surface, and additionally, it is passed through the through-hole 5 of the stent 1 so as to be directed from the outer peripheral surface to the inner peripheral surface. The freely insertable and removable distal end portion 40a of the stilet 40 which is passed through the pusher tube 10 and reaches the hollow portion of the stent 1 is inserted in the loop 3.

In this embodiment like the first embodiment described above, it is possible to pull the distal end side of the filament 30, the connection of which between the stent 1 and the pusher tube 10 has been released, proximally of the pusher tube 10 by moving the stilet 40 proximally.

Fifth Embodiment

Figure 32:
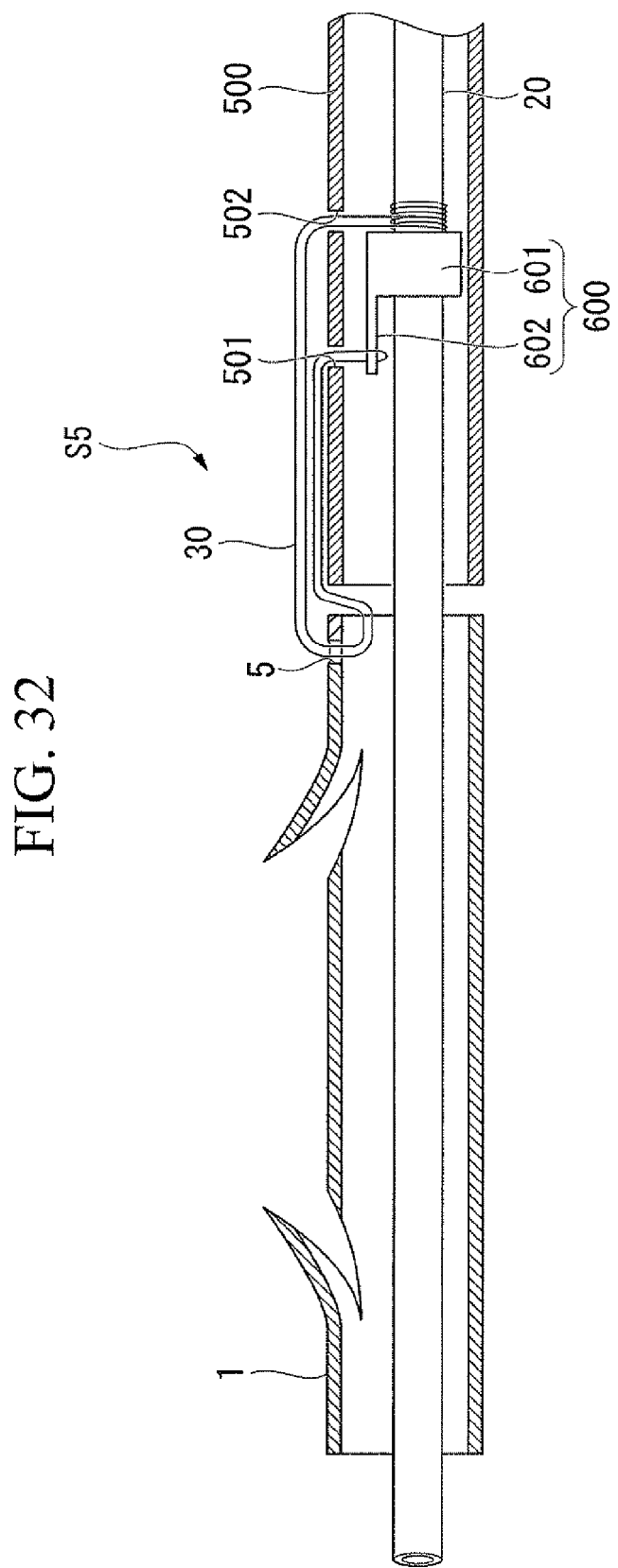
FIG. 32 is a cross-sectional view of the main portion which shows a fifth third embodiment of the stent delivery system of the present invention.

A fifth embodiment of the stent delivery system of the present invention shall be described with reference to FIG. 32.

The difference point of the stent delivery system S5 of the present embodiment with the stent delivery system S1 of the first embodiment described above is to have the proximal end side of the filament 30 fixed to the guide catheter 20, the way how the filament 30 which connects the stent 1 with the pusher tube 500 is passed through, and to have the engaging member 600, which engages the loop 31 of the filament 30 which connects the stent 1 and the pusher tube 500, attached to the guide catheter 20.

In short, the proximal end side of the filament 30 is fixed, for example, with glue in the condition to be wrapped around the guide catheter 20, the loop 31 is passed through the second through-hole 502 of the pusher tube so as to be directed from the inner peripheral surface to the outer peripheral surface, and after that, it is passed through the through-hole 5 of the stent 1 so as to be directed from the outer peripheral surface to the inner peripheral surface, and after being protruded from the opening at the proximal end side of the stent 1 by being bent back proximally of the stent 1, it is passed through the first through-hole 501 of the pusher tube so as to be directed from the outer peripheral surface to the inner peripheral surface. On the other hand, a cylindrical portion 601 and an engaging member 600 which has a bar portion 602 which extends from the cylindrical portion 601 to the distal end side are attached to the guide catheter 20 under the condition that the cylindrical portion 601 is engaged with the guide catheter from the outside. In addition, the freely insertable and removable distal end of the bar portion 602 is passed through the loop 31 of the filament 30.

According to the stent delivery system S5 in the present embodiment, if the guide catheter 20 is moved proximally, the bar portion 602 of the engaging member 600 which moves with the guide catheter 20 integrally is pulled out of the loop 31 of the filament 30, and the engagement to the filament 30 is released. After that, the filament, the distal end side of which is fixed to the guide catheter, is pulled into the same direction as the movement of the guide catheter 20 proximally.

Sixth Embodiment

Figure 33:
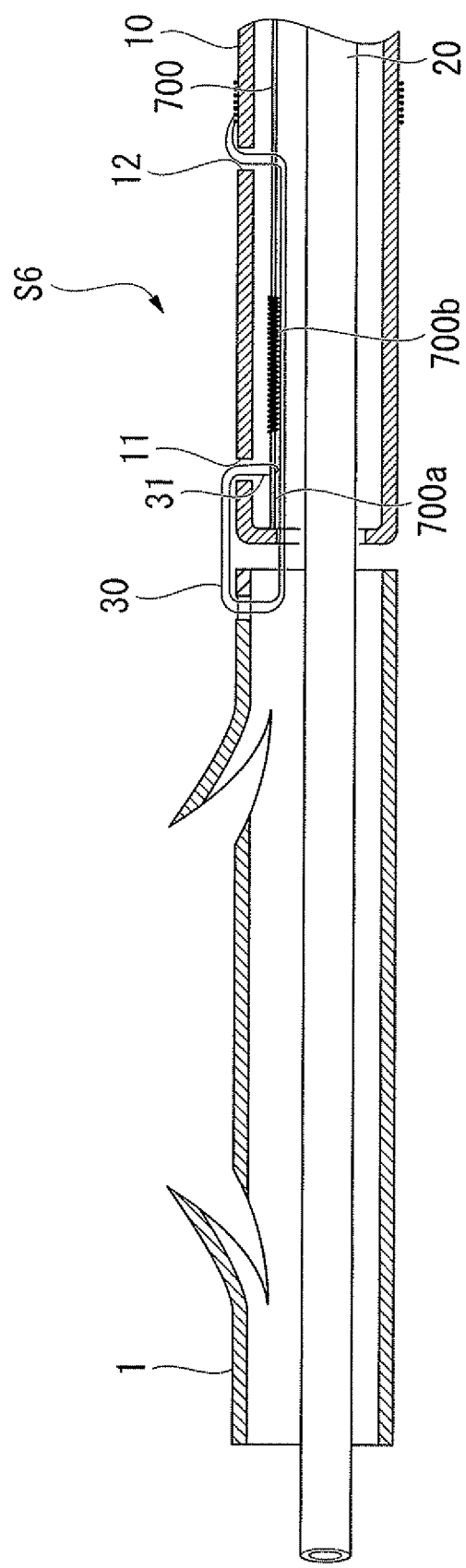
FIG. 33 is a cross-sectional view of the main portion which shows a sixth embodiment of the stent delivery system of the present invention.

A sixth embodiment of the stent delivery system of the present invention shall be described with reference to FIG. 33.

The difference point of the stent delivery system S6 of the present embodiment with the stent delivery system S1 of the first embodiment described above is to use the baculiform stilet 700.

In short, the stilet 700 is a baculiform member made of resin or metal, and the freely insertable and removable distal end portion 700a of the stilet 700 is inserted in the loop 31 at the distal end of the filament 30. In addition, the frictional portion 700b, which makes the stilet 700 stop to the filament 30 with friction by the process to make the outer peripheral surface rough or by the attachment of a material with high frictional coefficient or the like, is provided at the intermediate portion in the length direction of the stilet 700, concretely the portion which slightly turns from the distal end proximally and contacts with the filament 30 when it is set.

According to the stent delivery system S6 of the present embodiment, if the stilet 700 is moved proximally, the distal end portion 700a is pulled out of the loop 31 of the filament and the engagement with the filament 30 is released. In addition, the frictional portion 700b of the stilet 700 is also moved proximally, and the distal end of the filament 30 which is stopped frictionally by this frictional portion 700b is also pulled proximally of the guide catheter 20.

In the present embodiment, since the stilet 700 has a simple bar shape, the substantial outer diameter can be made small, and thereby the good movement of the stilet inside the pusher tube 10 can be secured.

Seventh Embodiment

Figure 34:
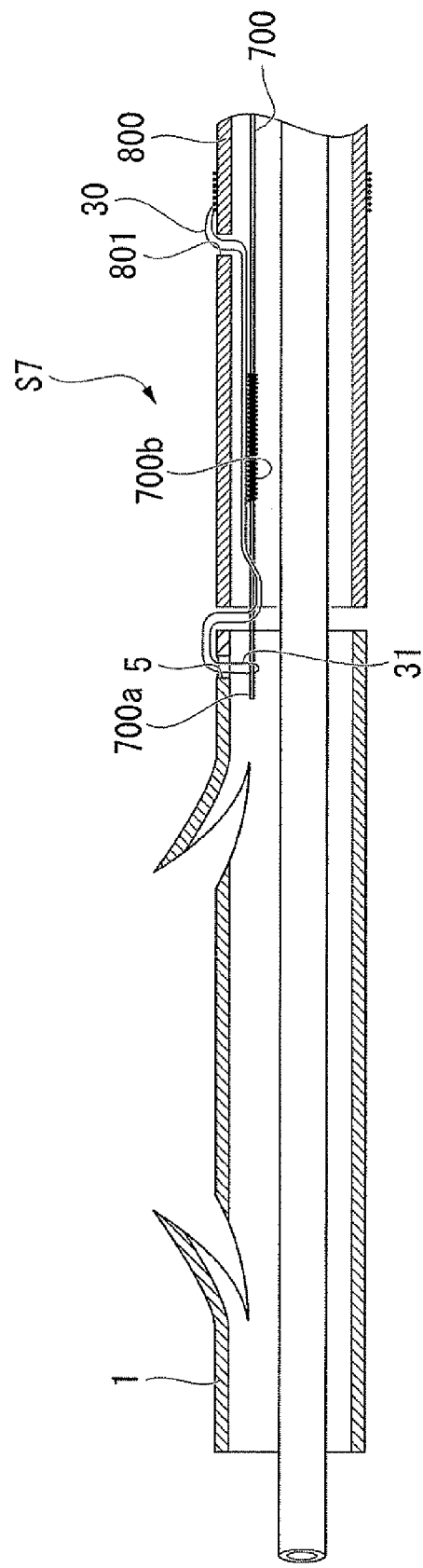
FIG. 34 is a cross-sectional view of the main portion which shows a seventh embodiment of the stent delivery system of the present invention.

A seventh embodiment of the stent delivery system of the present invention shall be described with reference to FIG. 34.

The difference point of the stent delivery system S7 of the present embodiment with the stent delivery system S6 of the sixth embodiment described above is the way how the filament 30 which connects the stent 1 with the pusher tube 800 is passed through, and that the distal end portion 700a of the stilet 700 is extended to the hollow portion of the stent 1 and is stopped to the loop of the filament 30 there.

In short, the loop 31 at the distal end of the filament 30, the proximal end side of which is fixed to the pusher tube 800, is inserted through the through-hole 801 of the pusher tube 800 so as to be directed from the outer peripheral surface to the inner peripheral surface, next it is protruded out of the opening of the distal end side of the pusher tube 800, and then it is inserted through the through-hole 5 of the stent 1 so as to be directed from the outer peripheral surface to the inner peripheral surface. On the other hand, the freely insertable and removable distal end portion 700a of the stilet is extended to the hollow portion of the stent 1, and is inserted in the loop 31 of the filament 30.

According to the stent delivery system S7 of the present embodiment, similar to the sixth embodiment described above, if the stilet 700 is moved proximally, the stop between the distal end portion 700a and the loop 31 can be released and the distal end side of the filament 30 can be pulled proximally of the pusher tube 20 by the frictional portion 700b.

Eighth Embodiment

Figure 35:
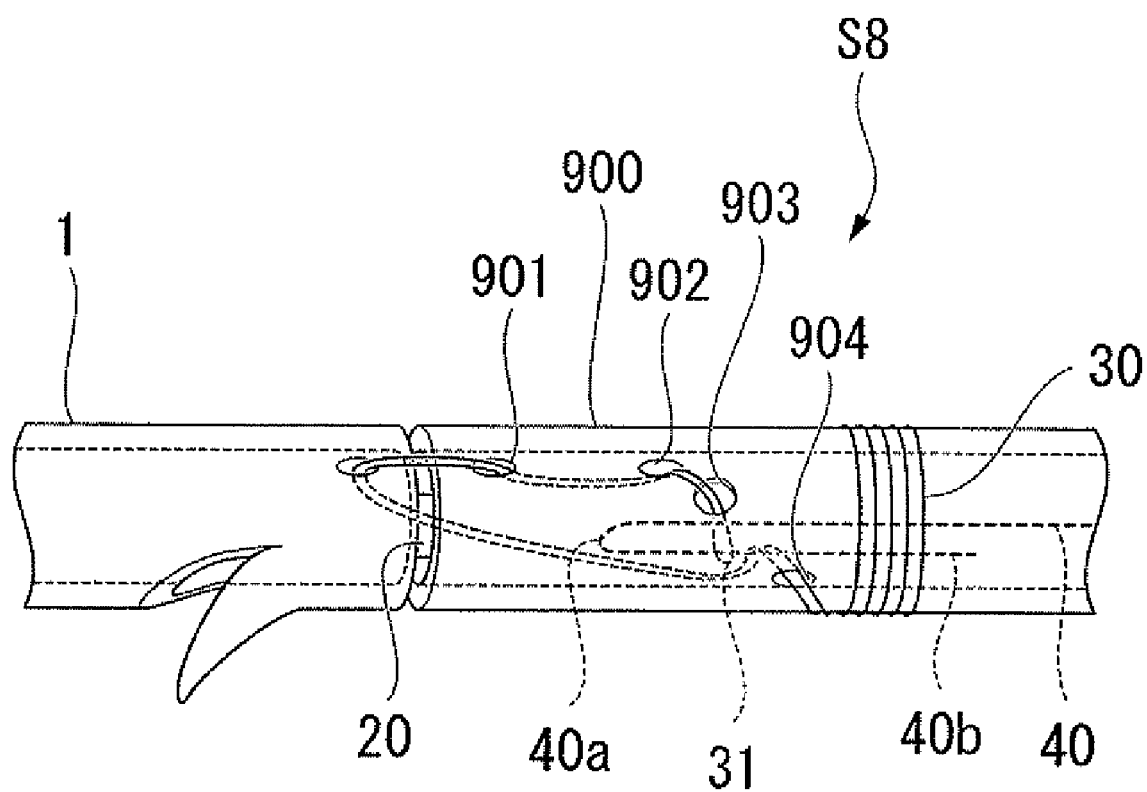
FIG. 35 is a perspective view of the main portion which shows the eighth embodiment of the stent delivery system of the present invention.

An eighth embodiment of the stent delivery system of the present invention shall be described with reference to FIG. 35.

The difference point of the stent delivery system S8 of the present embodiment with the stent delivery system S1 of the first embodiment described above is that the position where the distal end portion 40a of the stilet 40 is inserted and stopped in the loop portion 31 of the filament 30 is moved to the position which is more proximal than the distal end of the pusher tube 900.

In short, the first to the fourth through-holes 901, 902, 903, 904 are formed in the pusher tube 900 from the distal end proximally in order. The proximal end side of the filament 30 is wrapped around and fixed to the outer periphery of the pusher tube 900. The more distal side than the fixed portion of the filament 30 is first inserted through the fourth through-hole 904 so as to be directed from the outer peripheral surface to the inner peripheral surface. At that time, the distal end side of the filament 30 is inserted through the bent fold-over portion 40b of the stilet 40. Then, the distal end side of the filament 30 is inserted through the hollow portion of the pusher tube 900, the hollow portion of the stent 1 from the opening at the distal end side, and the through-hole 5 of the stent 1 so as to be directed from the inner peripheral surface to the outer peripheral surface and bent back there. In addition, the distal end side of the filament 30 is inserted through the first through-hole 901 of the pusher tube 900 so as to be directed from the outer peripheral surface to the inner peripheral surface, then the second through-hole 902 so as to be directed from the inner peripheral surface to the outer peripheral surface, and the third through-hole 903 so as to be directed from the outer peripheral surface to the inner peripheral surface. Then, in the hollow portion of the pusher tube 900, the freely insertable and removable bent distal end portion 40a of the stilet 40 is inserted through the loop portion 31 at the distal end of the filament 30.

Thus, the position of the engagement between the loop portion 31 of the filament 30 and the distal end portion 40a of the stilet 40 can be situated in the position which is more proximal than the distal end of the pusher tube 900 by the bent distal end portion 40a of the stilet 40 being inserted through the loop portion 31 at the distal end of the filament 30, which penetrates the third through-hole 903 from the outer peripheral surface to the inner peripheral surface, and being engaged. Thereby, it is possible to prevent the distal end 40a of the stilet 40 from being protruded from the distal end of the pusher tube 900 carelessly.

Note that if the distal end 40a of the stilet 40 is situated in the vicinity of the distal end of the pusher tube 900, the position of the distal end is changing by whether the path of the stilet 40 is in the inner diameter side (the curvature center side) of the pusher tube 900 or in the outer diameter side (the reverse side of the curvature center) in the bending portion when the stent 1 is delivered. For example, when the stilet is in the inner diameter side of the pusher tube 900, a problem that the distal end 40a of the stilet 40 is protruded from the distal end of the pusher tube 900 will happen. In addition, in the case that stilet 40 is used together with the guide catheter 20, the stilet 40 is sometimes moved to the distal end side as the movement of the guide catheter 20, and the distal end 40a of the stilet 40 is easier to be protruded from the distal end of the pusher tube 900.

In the eighth embodiment, it is possible to avoid with such an occurring problem.

Ninth Embodiment

Figure 36:
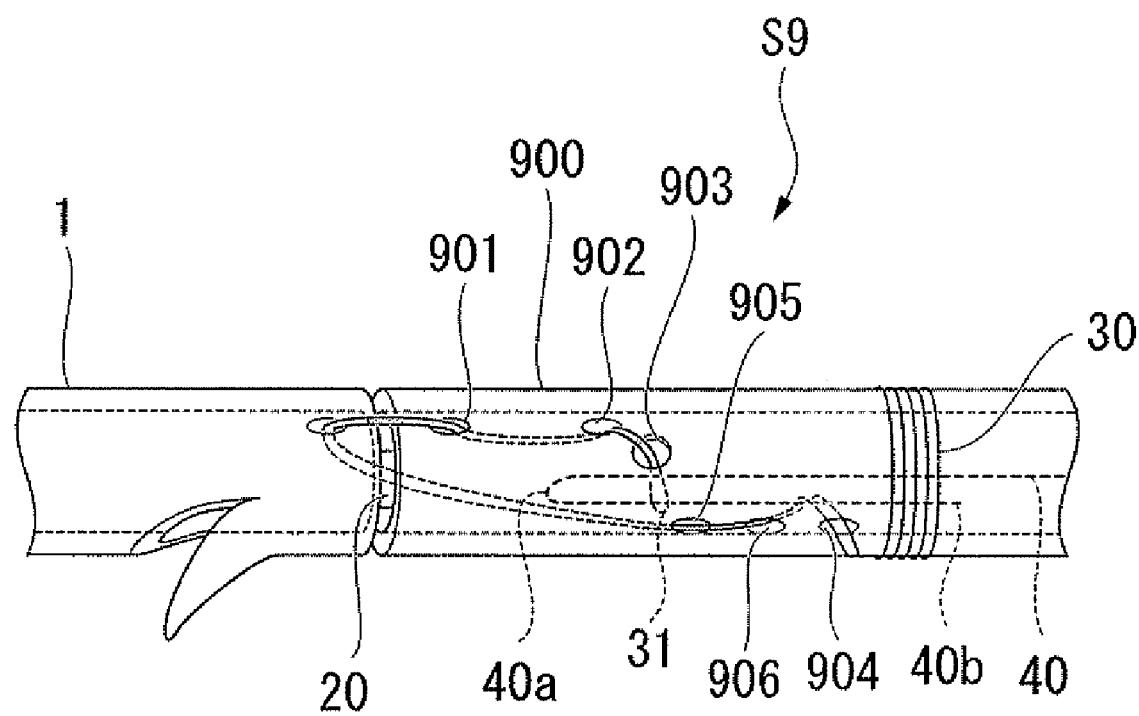
FIG. 36 is a perspective view of the main portion which shows a ninth embodiment of the stent delivery system of the present invention.

A ninth embodiment of the stent delivery system of the present invention shall be described with reference to FIG. 36.

The difference point of the stent delivery system S9 of the present embodiment with the stent delivery system S8 of the eighth embodiment described above is that two through-holes are added in the pusher tube 900.

In short, in the pusher tube 900, the fifth through-hole 905 and the sixth through-hole 906 are newly formed between the third through-hole 903 and the fourth through-hole 904 in order from the distal end side of the pusher tube 900.

The portion, which is stopped to the fold-over portion 40b of the stilet 40 after the filament 30 is passed through the fourth through-hole 904, is passed through the sixth through-hole 906 so as to be directed from the inner peripheral surface to the outer peripheral surface, and then, the distal end side of the filament 30 is passed through the fifth through-hole 905 so as to be directed from the outer peripheral surface to the inner peripheral surface.

In the stent delivery system S9 of the present embodiment, in addition to the effect that it is possible to prevent the distal end 40a of the stilet 40 from being protruded from the distal end of the pusher tube 900 carelessly as achieved in the stent delivery system of the eighth embodiment described above, the effect that it is possible to prevent the filament 30 from being interfered in the hollow portion of the pusher tube 900, the effect that the path (the stitch) of the filament 30 can be confirmed from the overviewed condition that the filament 30 is passed through the pusher tube 900, and the effect that thereby it is also possible to confirm whether the misassembly of the filament 30 exists or not.

While preferred embodiments of the invention have been described above, it should be understood that these are exemplary of the invention and are not to be considered as limiting. Additions, omissions, substitutions, and other modifications of the constitutions can be made without departing from the spirit or scope of the present invention.

In the embodiments described above, though the filament 30 is wholly used as a form of the double thread which is bent back at the center, it is not to be considered as limiting, and a form of the single thread in the whole filament and a loop formed only at the center may be used.

In addition, though the examples in which the stent is guided by using the guide catheter in the embodiments have been described above in the embodiments, the guide catheter is not always a necessary member, for example, in the case that a guiding portion with a smaller diameter than the main body of the tube is protruded and provided at the distal end of the pusher tube, and thereby the stent is guided coaxially, the guide catheter may not be used.

Furthermore, the form of the stilet is not limited in the filament, the distal end of which is bent, or baculiform, changes of the design can be made suitably.

What is claimed is:

1. A stent delivery system comprising:
   a tubular stent which is retainable in a body cavity of a living body;
   a guide catheter which is insertable in the tubular stent and which is insertable in the body cavity of the living body together with the tubular stent;
   a pusher tube, having a distal end edge face which contacts a proximal end edge face of the stent so that the proximal end edge face of the stent faces the distal end edge face of the pusher tube, the pusher tube pushes and moves the stent distally;
   a filament which connects the stent with the pusher tube by a proximal end of the filament being engaged with the pusher tube and by a distal end of the filament stretching toward the stent so as to penetrate a peripheral wall of the stent;
   an engaging member which is engaged with the distal end of the filament penetrating the peripheral wall of the stent, and which keeps the connection between the stent and the pusher tube by the filament; and
   a pulling member which pulls a distal end of the filament into a distal end of the pusher tube when the engagement between the engaging member and the filament is released and the connection between the stent and the pusher tube is released, wherein
   the engaging member and the pulling member comprise a single member,
   a distal end of the common member is a bent wire-like member forming a bent, overlapped portion, and the common member comprises a freely extendable and retractable stilet which is passed through a hollow portion of the pusher tube,
   a distal end of the bent overlapped portion of the stilet is inserted into a loop formed at the distal end of the filament so that the filament is wrapped around an outer circumference of the distal end of the bent overlapped portion, and
   a part of the filament is sandwiched in the bent overlapped portion of the stilet at the position of a more proximal side than the distal end of the bent overlapped portion around which a filament is wrapped.

2. The stent delivery system according to claim 1, wherein the guide catheter is freely extendable and retractable through the hollow portions of the stent and the pusher tube respectively, and guides the stent and the pusher tube along the axial direction, wherein the guide catheter is operable independently from the engaging member and the pulling member.

3. The stent delivery system according to claim 2, wherein a narrow portion which narrows an opening of the distal end of the pusher tube is formed, and a distal end portion of the stilet can be bumped against a wall portion of the narrow portion.

4. The stent delivery system according to claim 3, wherein a gap between an inner end of the narrow portion of the pusher tube and an outer surface of the guide catheter is set in a value which is larger than the outer diameter of the filament and is smaller than the outer diameter of the stilet.

5. The stent delivery system according to claim 2, wherein
   a first stopper is provided at a proximal end of the guide catheter;
   a second stopper which interferes with the first stopper is provided at a proximal end of the stilet; and
   the first stopper is arranged proximally relative to the second stopper.

6. The stent delivery system according to claim 2, wherein
   a first stopper is provided at a proximal end of the guide catheter;
   a second stopper which interferes with the first stopper is provided at a proximal end of the stilet; and
   the first stopper is arranged more distally relative to the second stopper.

7. The stent delivery system according to claim 1, wherein at least two through-holes are formed at a distal end portion of the peripheral wall of the pusher tube in order to pass the filament through the holes.

8. The stent delivery system according to claim 1, wherein at least three through-holes are formed at a distal end portion of the peripheral wall of the pusher tube in order to pass the filament through the holes.

9. The stent delivery system according to claim 1, wherein at least one through-hole is formed at a distal end portion of a peripheral wall of the pusher tube in order to pass the filament through the through-hole, and the filament is wrapped around so as to form a circle between the proximal end of the stent and the at least one through-hole formed in the peripheral wall.

* * * * *